(12) United States Patent
Bache et al.

(10) Patent No.: US 9,050,202 B2
(45) Date of Patent: Jun. 9, 2015

(54) ADJUSTABLE PROSTHETIC LIMB SYSTEM

(71) Applicant: OSSUR HF, Reykjavik (IS)

(72) Inventors: Andrew Bache, Reykjavik (IS); Michael Patrick Tuttle, Titusville, FL (US)

(73) Assignee: OSSUR HF, Reykjavik (IS)

( * ) Notice: Subject to any disclaimer, the term of this patent is extended or adjusted under 35 U.S.C. 154(b) by 0 days.

(21) Appl. No.: 13/930,053

(22) Filed: Jun. 28, 2013

(65) Prior Publication Data

US 2014/0005798 A1   Jan. 2, 2014

Related U.S. Application Data

(60) Provisional application No. 61/665,379, filed on Jun. 28, 2012.

(51) Int. Cl.
*A61F 2/80*  (2006.01)
*A61F 2/78*  (2006.01)
(Continued)

(52) U.S. Cl.
CPC ........... *A61F 2/80* (2013.01); *A61F 2002/5016* (2013.01); *A61F 2002/5026* (2013.01); *A61F 2002/5027* (2013.01);
(Continued)

(58) Field of Classification Search
CPC ... A61F 5/058; A61F 5/0525; A61F 5/05841; A61F 5/05858; A61F 5/05866; A61F 2/80; A61F 2/54; A61F 2/60; A61F 2/76; A61F 2/78; A61F 2/01; A61F 2/0102; A61F 2/02; A61F 2/058; A61F 2002/5081; A61F 2002/5083; A61F 2002/5084; A61F 2002/509; A61F 2002/543; A61F 2002/546; A61F 2002/5016; A61F 2002/5018; A61F 2002/502; A61F 2002/5038; A61F 2002/5026; A61F 2002/5027; A61F 2002/7862; A61F 2002/5039
USPC .................. 623/27–28, 30–36; 602/12, 16, 26
See application file for complete search history.

(56) References Cited

U.S. PATENT DOCUMENTS 37,282  A  *  1/1863  Engelbrecht .................... 623/38
51,593  A     12/1865  Jewett
(Continued)

FOREIGN PATENT DOCUMENTS

EP    1 433 447 A2   6/2004
GB    127 451 A      6/1919
(Continued)

OTHER PUBLICATIONS

Fillauer Socket Evaluation System. Fillauer catalog 2002.*
(Continued)

*Primary Examiner* — Thomas J Sweet
*Assistant Examiner* — Christie Bahena
(74) *Attorney, Agent, or Firm* — Workman Nydegger

(57) ABSTRACT

An adjustable socket system includes a distal end portion having an axis, and a frame having a plurality of elongate fingers longitudinally extending from the distal end portion. Each of the elongate fingers defines at least two segments pivotally connected to one another and extending in a longitudinal direction relative to the distal end portion. The at least two segments are pivotable inwardly or outwardly relative to the axis. At least one elongate element is adjustably connected to the plurality of elongate fingers and forms part of a circumference of the adjustable socket system.

9 Claims, 14 Drawing Sheets

(51) Int. Cl.
*A61F 2/76* (2006.01)
*A61F 2/50* (2006.01)

(52) U.S. Cl.
CPC .. *A61F 2002/7862* (2013.01); *A61F 2002/502* (2013.01); *A61F 2002/5039* (2013.01); *A61F 2002/509* (2013.01); *A61F 2/78* (2013.01); *A61F 2/76* (2013.01); *A61F 2/7812* (2013.01)

(56) References Cited

U.S. PATENT DOCUMENTS

| | | |
|---|---|---|
| 366,494 A | 7/1887 | Marks |
| 470,431 A | 3/1892 | Marks |
| 1,066,605 A | 7/1913 | Hanger |
| 1,144,681 A | 6/1915 | Apgar |
| 1,893,853 A | 1/1933 | Tullis |
| 2,229,728 A * | 1/1941 | Eddels ............... 623/36 |
| 2,634,424 A | 4/1953 | O'Gorman |
| 2,669,728 A | 2/1954 | Ritchie |
| 4,128,903 A * | 12/1978 | Marsh et al. ............... 623/36 |
| 4,161,042 A | 7/1979 | Cottingham et al. |
| 4,268,922 A | 5/1981 | Marsh et al. |
| 4,300,245 A | 11/1981 | Saunders |
| 4,459,709 A * | 7/1984 | Leal et al. ............... 156/60 |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,938,775 A | 7/1990 | Morgan |
| 4,988,360 A | 1/1991 | Shamp |
| 5,108,456 A | 4/1992 | Coonan, III |
| 5,133,777 A | 7/1992 | Arbogast et al. |
| 5,201,773 A | 4/1993 | Carideo, Jr. |
| 5,201,775 A | 4/1993 | Arbogast et al. |
| 5,246,464 A | 9/1993 | Sabolich |
| 5,312,669 A | 5/1994 | Bedard |
| 5,425,782 A | 6/1995 | Phillips |
| 5,503,543 A | 4/1996 | Laghi |
| 5,529,575 A | 6/1996 | Klotz |
| 5,545,231 A | 8/1996 | Houser |
| 5,653,766 A | 8/1997 | Naser |
| 5,718,925 A | 2/1998 | Kristinsson et al. |
| 5,728,165 A | 3/1998 | Brown, Sr. |
| 5,824,111 A | 10/1998 | Schall et al. |
| 5,885,509 A | 3/1999 | Kristinsson |
| 5,888,215 A | 3/1999 | Roos et al. |
| 5,888,217 A | 3/1999 | Slemker |
| 6,368,357 B1 | 4/2002 | Schon et al. |
| 6,497,028 B1 | 12/2002 | Rothschild et al. |
| 6,500,210 B1 | 12/2002 | Sabolich et al. |
| 6,557,177 B2 * | 5/2003 | Hochmuth ............... 2/159 |
| 6,793,682 B1 | 9/2004 | Mantelmacher |
| 6,942,703 B2 | 9/2005 | Carstens |
| 6,991,657 B1 | 1/2006 | Price, Jr. |
| 7,105,122 B2 | 9/2006 | Karason |
| 7,172,714 B2 | 2/2007 | Jacobson |
| 7,240,414 B2 | 7/2007 | Taylor, Sr. |
| 7,288,116 B2 | 10/2007 | Ikeda |
| 7,344,567 B2 * | 3/2008 | Slemker ............... 623/33 |
| 7,402,265 B2 | 7/2008 | Jacobson |
| 7,488,349 B2 | 2/2009 | Einarsson |
| 7,727,284 B2 | 6/2010 | Warila |
| 7,985,192 B2 | 7/2011 | Sheehan et al. |
| 8,088,320 B1 | 1/2012 | Bedard |
| 8,303,527 B2 | 11/2012 | Joseph |
| 8,308,815 B2 | 11/2012 | McCarthy |
| 8,323,353 B1 | 12/2012 | Alley et al. |
| 8,414,658 B2 * | 4/2013 | Johnson et al. ............... 623/32 |
| 2002/0099450 A1 | 7/2002 | Dean, Jr. et al. |
| 2003/0181990 A1 | 9/2003 | Phillips |
| 2006/0009860 A1 | 1/2006 | Price, Jr. |
| 2006/0173391 A1 * | 8/2006 | Bodenschatz ............... 602/12 |
| 2007/0004993 A1 | 1/2007 | Coppens et al. |
| 2007/0078523 A1 * | 4/2007 | Kholwadwala et al. ........ 623/36 |
| 2007/0152379 A1 | 7/2007 | Jacobson |
| 2008/0269914 A1 | 10/2008 | Coppens et al. |
| 2009/0076625 A1 | 3/2009 | Groves et al. |
| 2009/0105844 A1 | 4/2009 | Ortiz |
| 2009/0287128 A1 | 11/2009 | Ingimundarson |
| 2010/0030344 A1 | 2/2010 | Hansen et al. |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0121464 A1 | 5/2010 | Mantelmacher |
| 2010/0191348 A1 | 7/2010 | Kettwig et al. |
| 2010/0274364 A1 | 10/2010 | Pacanowsky et al. |
| 2011/0035027 A1 | 2/2011 | McCarthy |
| 2011/0046528 A1 * | 2/2011 | Stevenson et al. ............... 602/16 |
| 2011/0071647 A1 | 3/2011 | Mahon |
| 2011/0114635 A1 | 5/2011 | Sheehan |
| 2011/0232837 A9 | 9/2011 | Ottleben |
| 2011/0320010 A1 | 12/2011 | Vo |
| 2012/0022667 A1 | 1/2012 | Accinni et al. |
| 2012/0041567 A1 | 2/2012 | Cornell |
| 2012/0101417 A1 | 4/2012 | Joseph |
| 2012/0101597 A1 * | 4/2012 | Bache ............... 623/33 |
| 2012/0143077 A1 | 6/2012 | Sanders et al. |
| 2012/0253475 A1 | 10/2012 | Kelley et al. |
| 2012/0271210 A1 | 10/2012 | Galea et al. |
| 2012/0271433 A1 | 10/2012 | Galea et al. |
| 2013/0123940 A1 | 5/2013 | Hurley et al. |
| 2013/0245785 A1 | 9/2013 | Accini et al. |

FOREIGN PATENT DOCUMENTS

| | | |
|---|---|---|
| WO | 91/16019 A1 | 10/1991 |
| WO | 98/12994 A1 | 4/1998 |
| WO | 2007/035875 A2 | 3/2007 |
| WO | 2008/116025 A2 | 9/2008 |
| WO | 2009093020 A2 | 7/2009 |
| WO | 2012/021823 A1 | 2/2012 |
| WO | 2013071308 A1 | 5/2013 |

OTHER PUBLICATIONS

David, Scott. Young Afghan amputee gets new arms. Mar. 28, 2011. The United States Army.*
Initial and Interim Prostheses [Retrieved from Internet on Feb. 11, 2013], <URL:http://www.ottobockus.com/cps/rde/xbcr/ob_us_en/08cat_4.pdf>. Published in Prosthetics Lower Extremities 2008, see contents page <URL:http://www.ottobockus.com/cps/rde/xbcr/ob_us_en/08cat_1.pdf> pp. 24-31.
International Search Report and Written Opinion issued in PCT/US2011/057043 dated Jan. 27, 2012, 10 pgs.
International Search Report from corresponding PCT Application No. PCT/US2013/048675, Oct. 9, 2013.

* cited by examiner

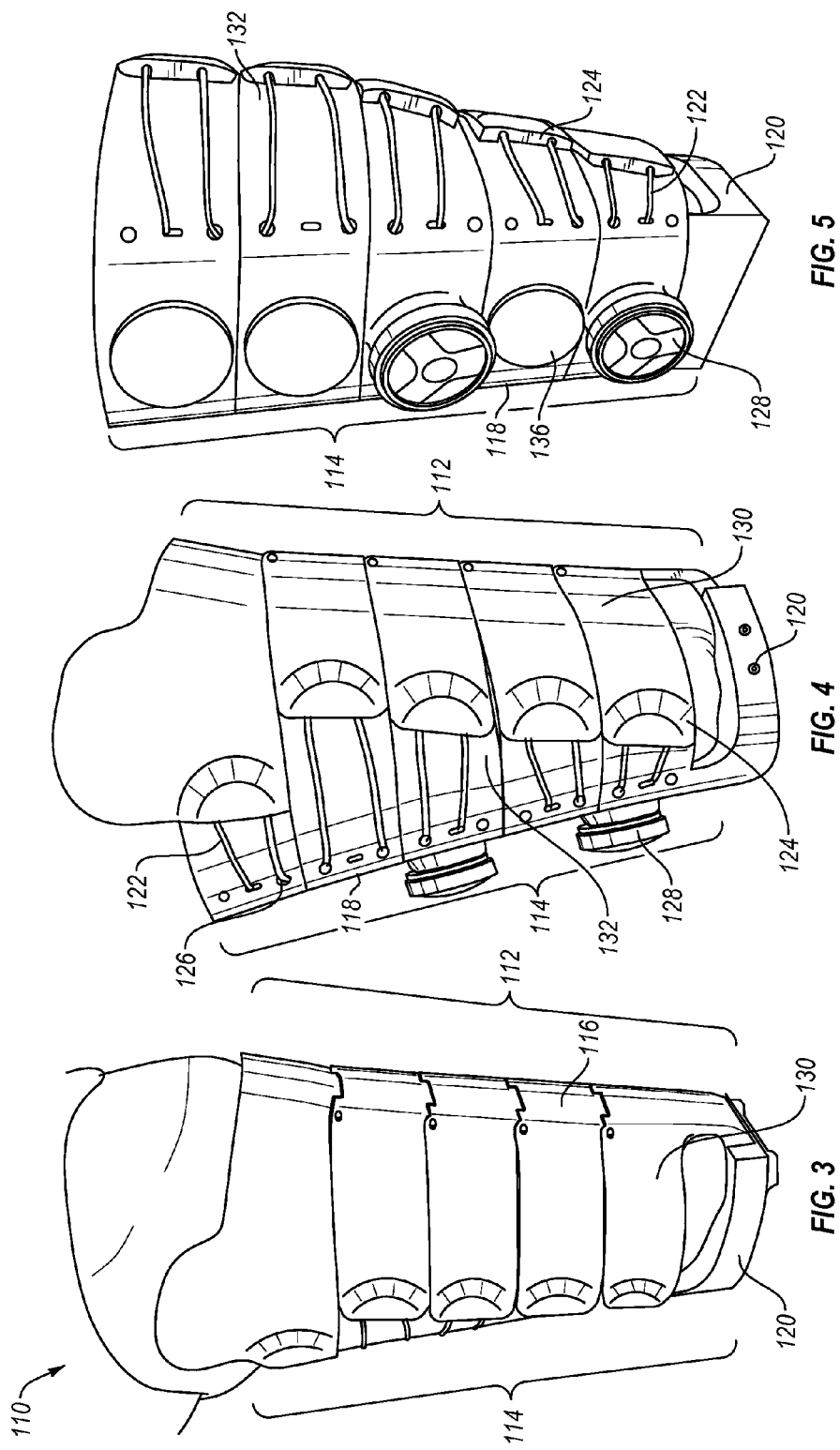

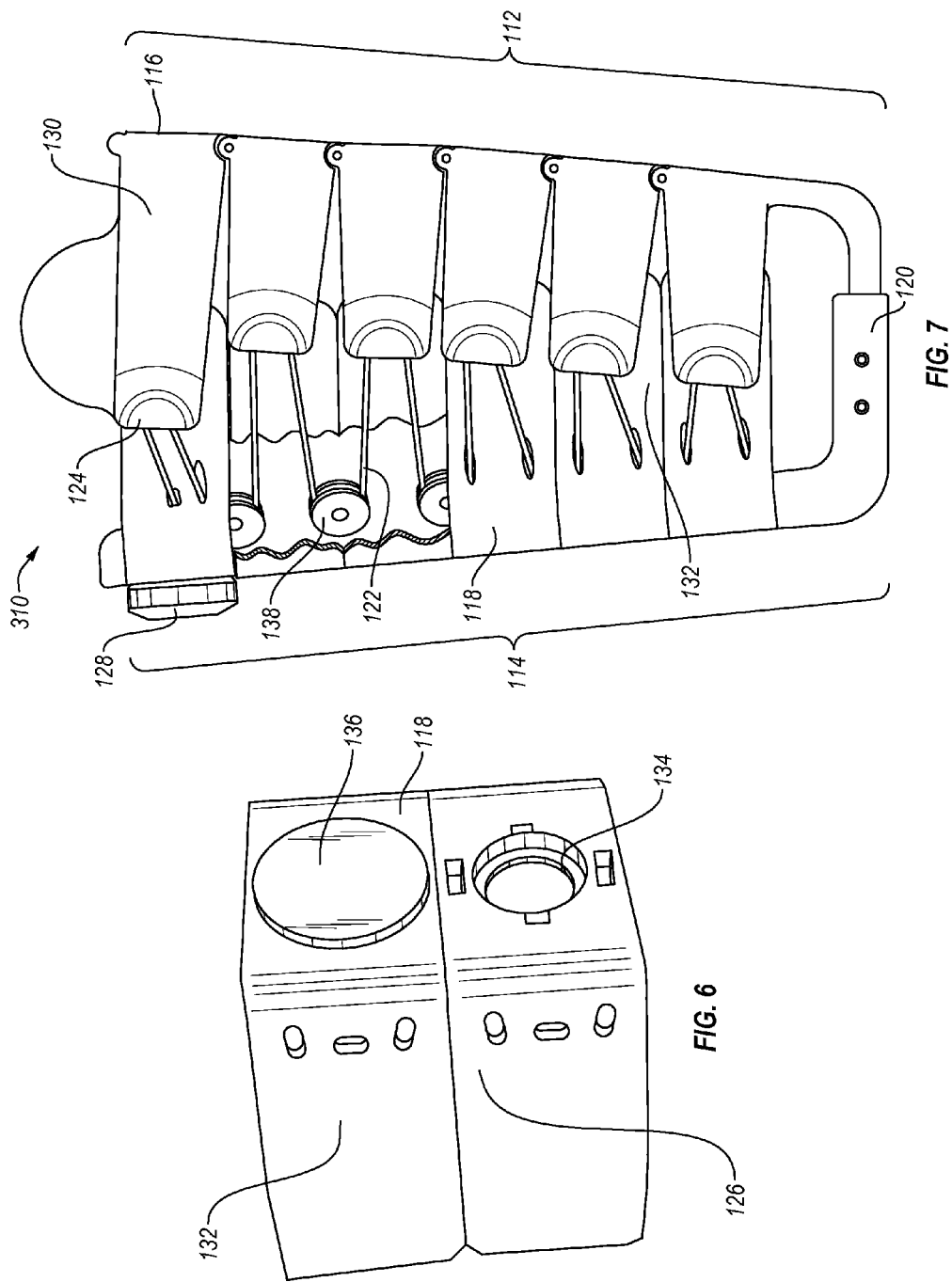

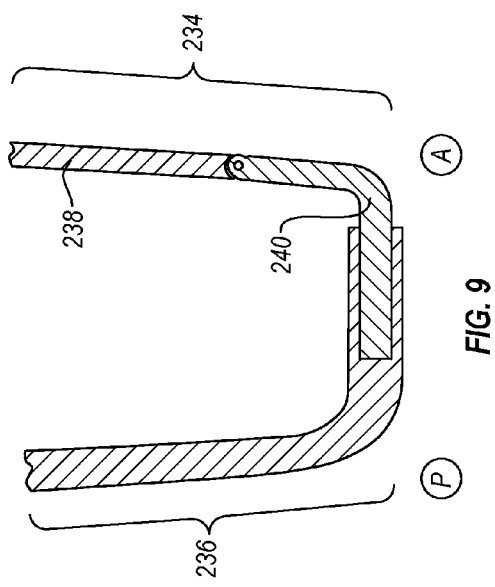
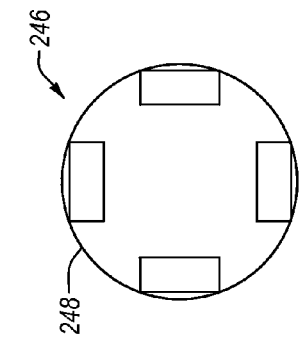
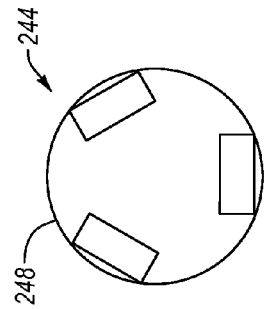
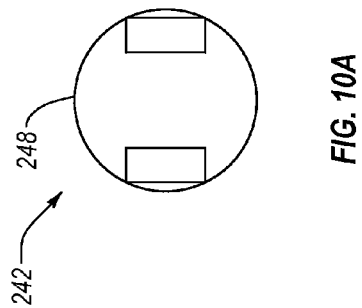

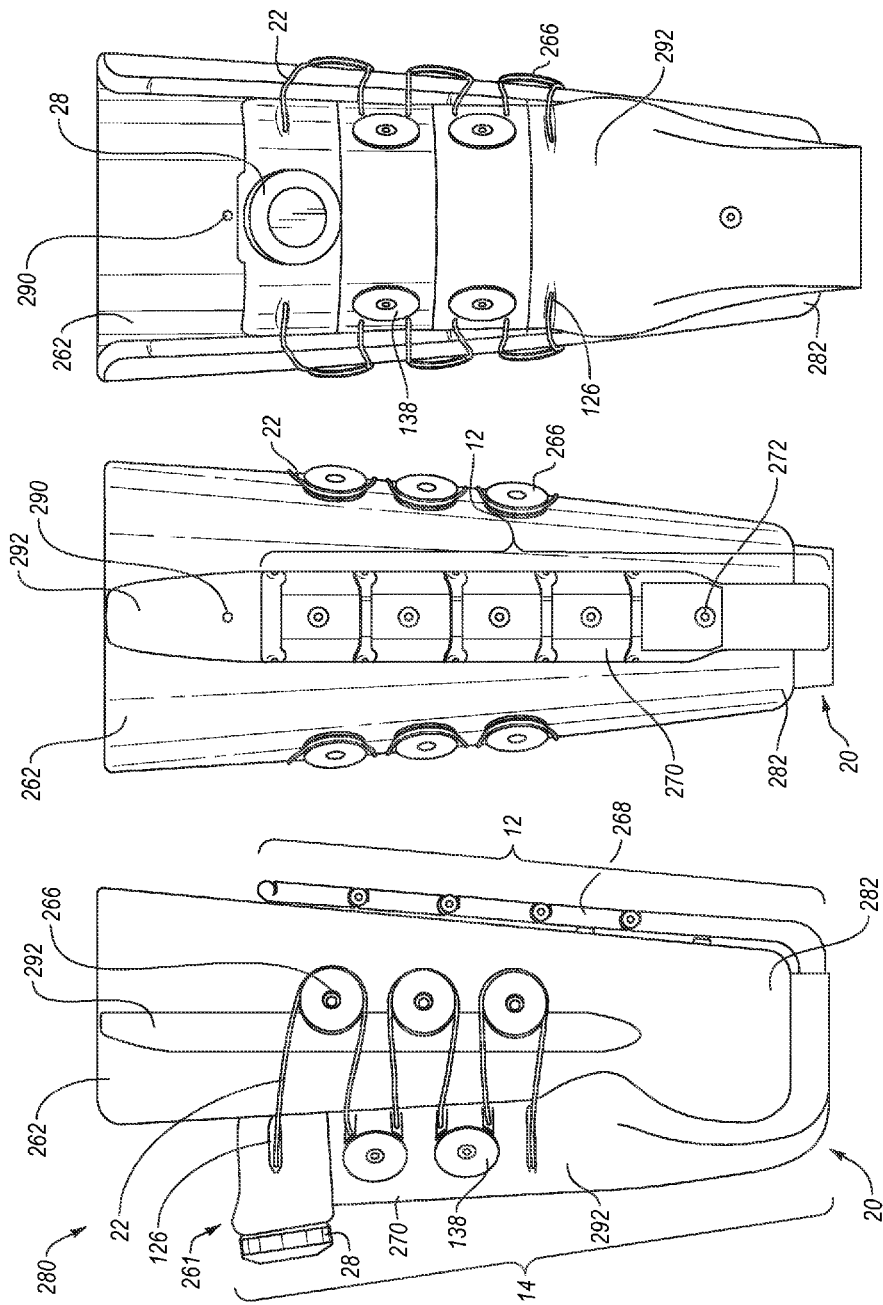

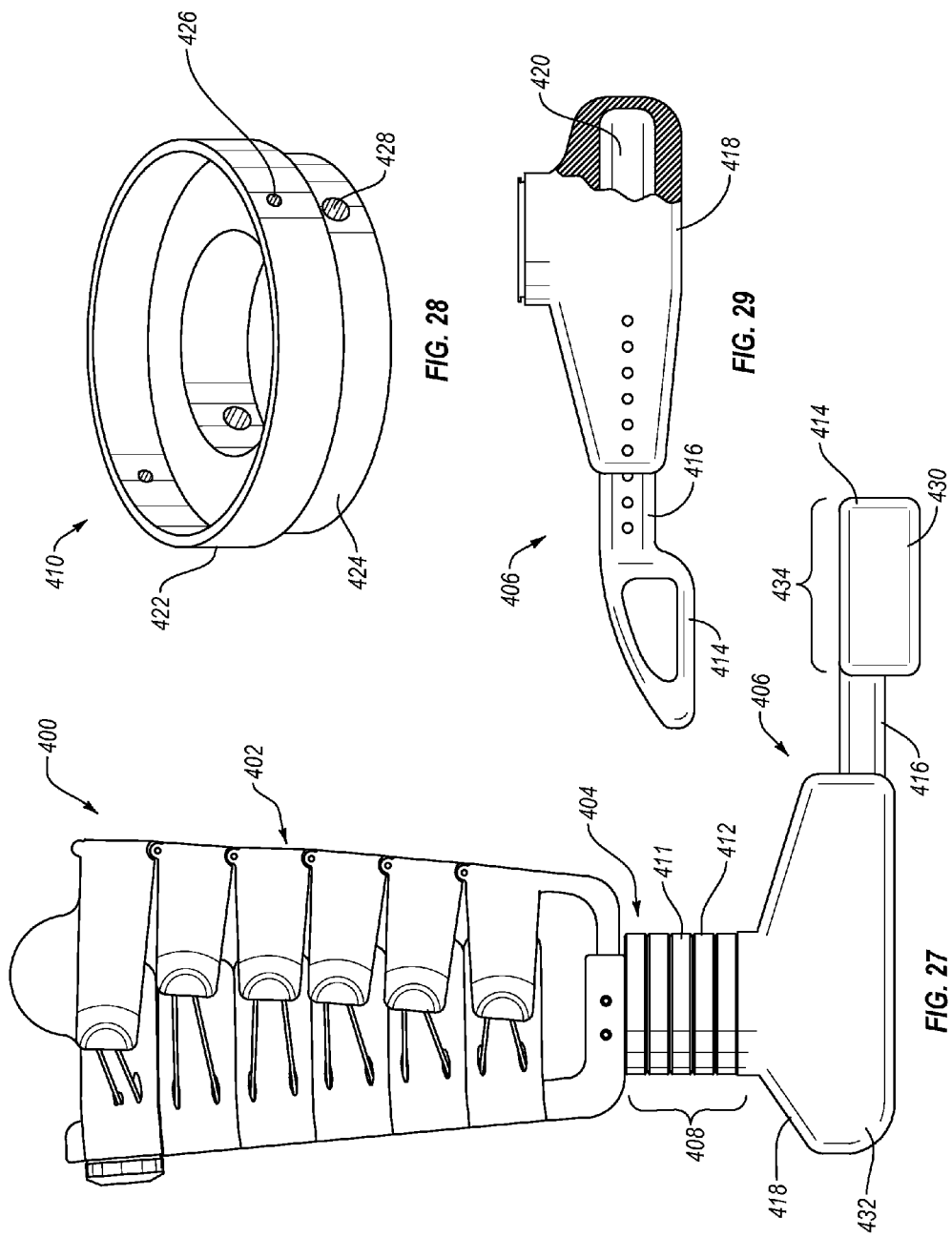

ADJUSTABLE PROSTHETIC LIMB SYSTEM

FIELD OF THE INVENTION

The invention relates to the field of prosthetic devices, and more particularly to an adjustable prosthetic limb system having an adjustable socket system for accommodating a residual limb, an adjustable pylon, and an adjustable foot.

BACKGROUND

A typical prosthetic leg and foot includes a socket, pylon, and foot. A socket is commonly referred to as the portion of a prosthesis that fits around and envelopes a residual limb or stump, and to which prosthetic components, such as a foot, are attached. When providing a socket to an amputee, it is essential to properly fit the socket and align various parts of the prosthesis to the amputee. Fitting and alignment of the socket and the parts are difficult tasks to perform, and require extensive knowledge, training and skill for the prosthetist.

Typically, sockets for definitive prostheses are customized for a residual limb of a wearer. According to one method, the sockets are formed over a model of the stump, such as one formed by plaster-of-Paris, to be used to distribute forces between the socket and the stump in a comfortable way to the amputee. In another method, the socket may be obtained from computer aided design by modeling the shape of the stump, and subsequently forming a model. Once the model is obtained in either of these methods, a socket is formed over the model by using fabric and liquid plastic resin to obtain a definitive rigid socket customized to a limb.

Proper fitting of a socket to the stump is critical to the success of the prosthesis. The socket must fit closely to the stump to provide a firm connection and support, but must also be sufficiently loose to allow for circulation. In combination with proper fitting, the socket must transfer loads from the residual limb to the ground in a comfortable manner.

Most prosthetic sockets are permanently formed to a customized shape that is static, meaning the socket does not account for shape and volume fluctuations of the residual limb. When there are shape and volume fluctuations, the fitting of the socket is impeded, with these sockets causing discomfort, pain and soft tissue breakdown of the stump. Conventional sockets tend to be bulky and cumbersome to wear, and may be difficult to don making the residual limb uncomfortable when worn.

As to methods of attaching the socket to the residual limb, conventional sockets rely on different mechanisms such as negative pressure or a friction or tension based interface. Conventional sockets may have poor force distribution on the residual limb causing a concentration of pressure on a certain area of the stump. This poor distribution of pressure causes pain, discomfort, and tissue breakdown. Conventional sockets generally are not breathable which results in undesirable temperature and humidity within the socket.

For certain types of amputations such as disarticulation amputations where the limb is separated at a joint, it is difficult to create sockets which are not bulky and provide use of the natural anatomy. Conventional sockets for disarticulation amputations use a rigid socket which requires that the opening for the socket be larger than the joint to allow for donning and doffing. The rigid sockets generally have a general uniform shape which receives a large portion of the residual limb and the space between the residual limb and the interior of the rigid socket wall is filled in with a soft or cushioning material.

Besides the socket, a leg prosthesis includes a prosthetic foot and depending on the level of the amputation, a pylon between the socket and the foot. The length of the pylon must also be customized for the amputee's height and level of amputation. A prosthetist aligns the pylon, the socket, and the foot to minimize undesired forces produced during gait on the user and prosthesis and to provide the user with a more symmetric gait. The alignment of the prosthesis also affects the pressure distribution at the stump and socket interface.

It is desirable to provide a simplified and compact prosthesis system that overcomes the drawbacks over known prosthesis systems. Particularly, it is advantageous to provide a complete prosthetic limb system that is off-the-shelf and capable of accommodating a variety of residual limb sizes. It is also desired a socket system of the prosthetic limb system be adjustable to allow for volume and shape fluctuations, and in effect, provide a dynamic socket as opposed to the known static sockets. The adjustable socket can better adjust for pressure distribution, and maintain comfort to the amputee over a range of care and residual limb conditions. It is further desired that the pylon and the foot of the prosthesis be adjustable to accommodate a variety of users and gaits.

According to an embodiment, the adjustable socket system has a distal end portion having an axis, and a frame has a plurality of elongate fingers longitudinally extending from the distal end portion. Each elongate finger defines at least two segments pivotally connected to one another and extending in a longitudinal direction relative to the distal end portion. The at least two segments are pivotable inwardly or outwardly relative to the axis. At least one elongate element connects to the plurality of elongate fingers and forms part of a circumference of the adjustable socket system in combination with the fingers of the frame. The fingers may be formed from a flexible material such as resin reinforced with carbon fibers.

The distal end portion may define a plurality of base elements extending laterally and extending longitudinally in part to couple to a respective one of the segments of each of the plurality of fingers. The distal end part has a proximal contour adapted to receive a distal end of a residual limb, and sized to accommodate a large variety of differently shape residuums. The plurality of base elements may be rigidly secured to the respective one of the segments of each of the plurality of fingers.

A sleeve has a plurality of pockets wherein each of the pockets extends over a respective one of the plurality of fingers. The sleeve carries the at least one elongate element. The sleeve may be formed from an inelastic textile. The at least one elongate element includes a lace slidably connecting to each of the plurality of pocket, and the at least one elongate element may be a textile lace that is inelastic. Each of the pockets may be slidably removable from the respective one of the plurality of fingers.

According to a variation, the at least one tensioning device is connected to the frame and the at least one elongate element connects to the plurality of fingers to form at least part of the circumference of the socket system. The at least one tensioning device is mounted to the distal end portion below the frame. The at least two segments define a plurality of channels for directing the at least one elongate element along a surface of the at least two segments. The at least two segments define opposed apertures corresponding to opposed side walls and in communication with a respective one of the plurality of channels. The at least one elongate element extends through the opposed apertures.

According to another variation, the at least one elongate element has at least one end adjustably secured to the distal end portion. Adjustment of the at least one elongate element is arranged to change tension in the at least one element.

In another embodiment, an adjustable prosthetic socket system has first and second opposed sides, and includes a socket frame having a first component arranged along a first side of the socket system and a second component arranged along a second side of the socket system. The first component is connected to the second component. A tubular insert is arranged on the interior of the socket frame forming an interior surface of the socket system. At least one tensioning element connects the circumferential insert to at least one of the first component and the second component. At least one tensioner is attached to the at least one tensioning element that draws in and releases the tensioning element to adjust the circumference of at least one area of the socket system. A partial enclosure may laterally extend from each side of the first component.

The adjustable prosthetic socket system may also include a plurality of tensioning element guides arranged longitudinally between the first component and the second component. The at least one tensioner is attached to the second component and the at least one tensioning element connects the plurality of tensioning element guides to the second component. The plurality of tensioning element guides is connected to the tubular insert and the partial enclosure. The first component is an adjustable spine, the second component is a rigid spine, and the tubular insert is flexible.

Other embodiments are presented below in accordance with the description and various drawings.

BRIEF DESCRIPTION OF THE DRAWINGS

The inventive adjustable prosthetic limb system is described referring to the accompanying drawings that show preferred embodiments according to the system described. The system as disclosed in the accompanying drawings is illustrated for example only. The elements and combinations of elements described below and illustrated in the drawings can be arranged and organized differently to result in embodiments still within the spirit and scope of the device described.

FIG. 3 is an elevational view of the anterior of another embodiment of the adjustable socket system.

FIG. 4 is an elevational view of the embodiment of the adjustable socket system of FIG. 3.

FIG. 5 is an elevational view of the posterior of the adjustable socket system of FIGS. 3 and 4.

FIG. 6 shows two adjacent rigid vertebrae of the embodiment of the adjustable socket system in FIGS. 3-5.

FIG. 7 is an elevational view of another embodiment of the adjustable socket system.

FIG. 9 is a schematic illustration of an embodiment of the adjustable socket system having a rigid posterior spine and a rigid anterior spine having one articulation point.

FIG. 10A is a schematic top view of an embodiment of the adjustable socket system having two spines.

FIG. 10B is a schematic top view of an embodiment of the adjustable socket system having three spines.

FIG. 10C is a schematic top view of an embodiment of the adjustable socket system having four spines.

FIG. 15 is an elevational side view of a side of another adjustable socket system having a socket frame and tubular insert.

FIG. 16 is an elevational view of the anterior side of the adjustable socket system in FIG. 15.

FIG. 17 is an elevational view of the posterior side of the adjustable socket system in FIGS. 15 and 16.

FIG. 27 is an elevational view of an embodiment of an adjustable prosthetic limb system having an adjustable socket system, an adjustable pylon, and an adjustable prosthetic foot.

FIG. 28 is a perspective view of an embodiment of a stacking component of the adjustable pylon in FIG. 27.

FIG. 29 is an elevational view of an embodiment of an adjustable prosthetic foot.

DETAILED DESCRIPTION OF VARIOUS EMBODIMENTS

A. Overview

Figure 1:
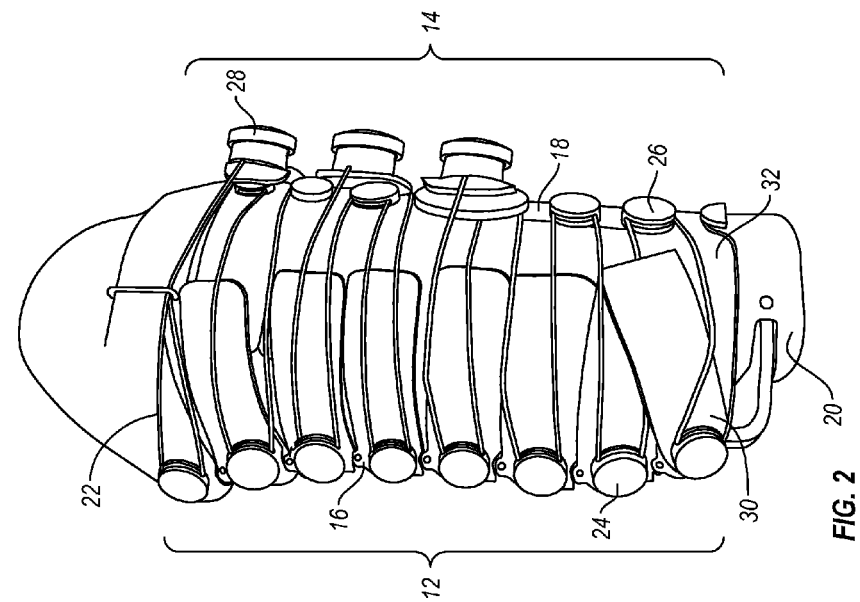
FIG. 1 is a front elevational view of an embodiment of the adjustable socket system.

A better understanding of different embodiments of the invention may be had from the following description read with the accompanying drawings in which like reference characters refer to like elements.

While the disclosure is susceptible to various modifications and alternative constructions, certain illustrative embodiments are in the drawings and will be described below. It should be understood, however, there is no intention to limit the disclosure to the specific embodiments disclosed, but on the contrary, the intention covers all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

The anatomical terms described are not intended to detract from the normal understanding of such terms as readily understood by one of ordinary skill in the art of prosthetics. The term "distal" is used to denote the portion or end of a limb farthest from the central portion of the body. The term distal is the opposite of "proximal" which is used to denote that the end or portion of the limb is nearer to the central portion of the body.

Some components described share similarities to components in U.S. Pat. Nos. 7,488,349, 7,867,286 and U.S. publication no. 2012/0101597, incorporated by reference and belonging to the assignee of this disclosure.

B. Embodiments of the Adjustable Prosthetic Limb System

Embodiments of the adjustable prosthetic limb system will be described herein which comprise a socket, pylon, and prosthetic foot. The adjustable prosthetic limb system is advantageous in that components of the adjustable prosthetic limb system are adjustable and therefore customizable to the user's need and preferences. It is preferred that at least the prosthetic socket is adjustable in the adjustable prosthetic limb system.

Besides using a socket adjustable to the physical features of a residual limb, it also advantageous to have a prosthetic limb which has other adjustable components. The adjustable socket system, such as the embodiments described, may be used with an adjustable pylon and adjustable prosthetic foot to provide the user with a fully adjustable prosthetic limb system. The skilled person would also understand that the embodiments of the adjustable pylon and prosthetic foot as described may be used with a variety of sockets and are not limited to being used with an adjustable socket. The adjustable pylon and prosthetic foot may be used with a suspension socket.

Embodiments of the adjustable prosthetic limb system described are advantageous in that the embodiments of the adjustable prosthetic limb system enable the user to simultaneously adjust the horizontal position of the socket regarding the prosthetic limb, the vertical position of the socket regarding the prosthetic limb, and the angle of the socket regarding the prosthetic limb. The prosthetic foot is furthermore adjustable. The adjustable prosthetic limb system as described provides an off-the-shelf prosthetic limb that delivers a complete, instant prosthesis solution when an amputee has an urgent need for an artificial limb and that can be adapted to a wide range of user needs and preferences.

1. Embodiments of the Adjustable Socket System

The embodiments of the adjustable socket system described are adapted to receive and fit a range of heights and lengths of a residual limb, and accommodate volume and shape fluctuations of a residual limb. From its versatility in fitting and adjustment, and its breathability, the adjustable socket system can decrease pain, discomfort and soft tissue breakdown over known sockets static in size and shape.

The versatility in fitting and adjustment and breathability of the embodiments of the adjustable socket system described is partially attributable to the socket system having an adjustable surface to accommodate specific residual limb shapes which will be described in more detail regarding specific embodiments. To achieve this adjustability, the socket system may have the form of a rigid weight bearing structure adapted to partially surround the residual limb and a flexible structure to support the remaining portion of the residual limb. The flexible structure may be a flexible material such as the tensioning element and/or lateral flaps described below or the system of straps described in U.S. publication no. 2012/0101597. The flexible structure can form the anterior or posterior of the socket system. Meanwhile, the rigid weight bearing structure is also adjustable such that portions of the weight bearing structure may be removed, added, or exchanged with components having different properties.

Figure 2:
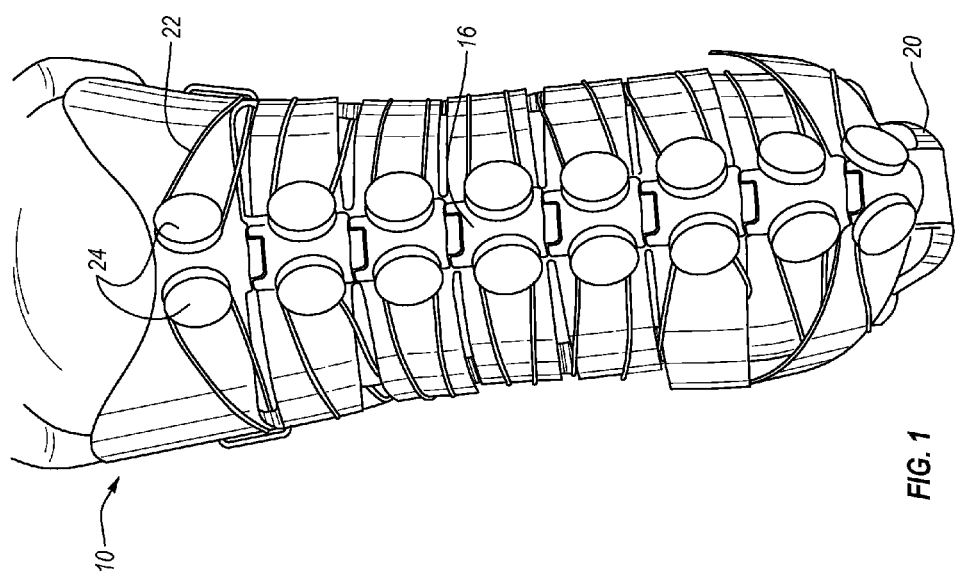
FIG. 2 is an elevational view of the embodiment of the adjustable socket system of FIG. 1.

Under an embodiment of the invention, FIGS. 1-2 illustrate an adjustable socket system 10 configured to receive a residual limb from a transtibial level amputation. It will be understood, however, that the adjustable socket system may be adapted to receive a variety of types of amputations, whether configured for the leg or arm.

Turning to the details of the socket system 10, the socket system 10 has a flexible spine 12 on the anterior side of the socket system 10 and a rigid spine 14 on the posterior side of the socket system 10. Each spine 12, 14 is formed of a plurality of connected vertebrae 16, 18. The vertebrae 16 of the flexible spine 12 can pivot relative to each other to provide the spine 12 with flexibility to adapt to the shape of the residual limb. The vertebrae 18 of the rigid spine 14 are non-pivoting. The socket system 10 also includes a distal base 20.

The socket system 10 is attached to the residual limb using a friction or tension based interface in a tensioning system. In the socket system 10 in FIGS. 1 and 2, the tensioning system comprises at least one tensioning element 22, tensioning element guides 24, 26, and at least one tensioner 28. The tensioning element 22, which is shown as a cable or wire, is looped around tensioning element guides 24, 26 provided on the exterior of both sides of each vertebrae 16, 18. The tensioning element guides 24, 26 may take the form of a circular pin as shown in FIGS. 1 and 2. Any other means known in the art of holding the tensioning wire in place may be used such as a hook or a ring.

The anterior tensioning element guides 24 and the posterior tensioning element guides 26 are offset to loop the cable 22 around the guides 24, 26 in a zigzagging fashion along the length of the socket system 10 and essentially wrap the residual limb into the socket system 10. The cable 22 and the guides 24, 26 form a pulley-like system for tightening and loosening the adjustable socket system 10 which enables simple tension adjustment along the entire socket system 10. The socket system 10 has a conical or tubular shape, and the cable 22 defines the outer periphery of the socket system 10 and therefore, the circumference of the socket system 10 at various points.

The length of the cable 22 and the pressure applied to the residual limb may be adjusted using one or more tensioners 28. The tensioners may be turned one direction to increase the length of cable 22 and turned a second direction to decrease the length of cable 22.

In the illustrated embodiment of FIGS. 1 and 2, the flexible vertebrae 16 and rigid vertebrae 18 may be approximately the same height to produce a one-to-one correspondence between the vertebrae 16, 18 in the flexible spine 12 and rigid spine 14. To offset the tensioning element guides 24, 26, the anterior tensioning element guide is completely formed and placed on one anterior vertebra 16, and the posterior tensioning element guide 26 is formed of two pieces.

A complete posterior tensioning element guide 26 is formed by one piece on a posterior vertebra 18 and a corresponding piece on an adjacent posterior vertebra 18. Alternatively, the anterior tensioning element guide may be formed of two pieces. The guides 24, 26 are shown as pins in FIGS. 1 and 2 on the exterior of the vertebrae, and the guides 24, 26 may also be formed as interior passageways of the vertebrae. The number of vertebrae 16, 18 used in the flexible spine 12 and the rigid spine 14 may be varied by removing or adding individual vertebrae to easily adjust the height of the spines 12, 14 and obtain a customized fit.

The cable 22 may be formed of more than one cable with tensioners 28 arranged to adjust the cable length of certain cables. Through this tensioning system arrangement, the adjustable socket system 10 has a regional circumference adjustment with each tensioner 28 arranged to adjust the tension or circumference of specific areas of the socket system 10 to enable adjustment for a tailored fit of the adjustable socket system 10 to the residual limb. FIG. 2 shows the use of three tensioners 28.

Using multiple tensioners allows for different tension in different areas or sides of the socket system 10. One tensioner may adjust the circumference or tension of the proximal area of the socket system 10 while another tensioner adjusts the circumference or tension of the distal area of the socket system 10. As depicted in FIG. 2, the tensioners 28 may be mounted on the posterior side of the posterior vertebrae 18.

The socket system 10 may include a material placed between the cable 22 and the residual limb to which the pressure produced by tension in the cable 22 is applied. In this embodiment, lateral or horizontal flaps 30, 32 are attached or incorporated into the vertebrae 16, 18 of the spines 12, 14. The lateral flaps 30, 32 extend part way on each side of the vertebrae 16, 18 between the spines 12, 14 as shown in FIG. 2. The lateral flaps 30, 32 preferably have a length which allows for some overlap when worn on a residual limb.

As shown in FIGS. 1 and 2, the vertebra at the proximal end of the flexible spine 12 may have condylar wings instead of lateral flaps to provide for condylar support of the residual limb. A vertical tab may be provided between the condylar wings above the proximal anterior vertebra to reduce occurrences of hyperextension of the knee. In another embodiment, the material between the cable 22 and the residual limb are vertical flaps extending proximally from the distal base 20. Since flaps are used on the vertebrae 16, 18, the socket system 10 is a breathable socket while still providing additional support around the sides of the socket system 10.

Besides having an adjustable peripheral surface, the distal base 20 may be formed of two components to have an adjustable length to accommodate smaller or larger residual limbs as described in U.S. publication no. 2012/0101597.

Each anterior vertebra 16 in the flexible spine 12 may have a proximal connector and distal hinge connector as described in U.S. publication no. 2012/0101597 to attach each anterior vertebra 16 to each other. Each posterior vertebra 18 in the rigid spine 14 may have a pair of proximal posts and distal posts as described in U.S. publication no. 2012/0101597 to attach each posterior vertebra 18 to each other.

Similar to the embodiment illustrated in FIGS. 1 and 2, the socket system 110 in FIGS. 3-5 has a flexible spine 112 and a rigid spine 114 also formed of a plurality of vertebrae 116, 118 and an adjustable distal base 120. The vertebrae 116, 118 have lateral flaps 130, 132.

The socket system 110 has a tensioning element or cable 122 used to adjust the circumference or outer peripheral surface of the socket system 110. The socket system 110 incorporates the tensioning element guides into the interior of the vertebrae or the lateral flaps. As is shown in FIGS. 4 and 5, the cable 122 passes through an anterior guide 124 on the posterior end of each anterior lateral flap 130. For the rigid spine 114, a posterior guide 126 for the cable 122 is in an interior passageway which extends through multiple posterior vertebrae 118. To reach the posterior guide 126, the cable 122 passes through an opening and an interior passageway and exits through another opening of the posterior vertebra 118. The posterior vertebrae 118 may furthermore be provided with over two openings for better adjustment.

The lateral flaps 130, 132 are preferably formed to minimize any gaps between adjacent flaps and maximize surface area of the socket system 110 in contact with the residual limb or prosthetic liner to provide a stronger attachment and better pressure distribution. Material may also be added between the lateral flaps to prevent gaps between adjacent lateral flaps. The lateral flaps may be incorporated into the vertebrae as a single continuous component or may be removable. The lateral flaps preferably have an arcuate shape to conform more closely to the shape of the residual limb and are made of a breathable material such as a textile.

Placing the tensioners 128 of the socket system 110 is customizable as well. Each posterior vertebra 118, which is in more detail in FIG. 6, has a recess 134 into which the tensioner 128 may be inserted and removed. The winding of the tensioner 128 is inserted into the recess 134 and the tensioner is locked into the vertebra 118 using various mechanical locking mechanisms as known in the art. The posterior vertebra 118 has side openings for the internal tensioning element guide through which the cable 122 passes. Having removable tensioners 128 allows the user or fitter to determine the number of tensioners 128 and cable combinations to use and the arrangement of each tensioner 128 and cable 122. Unused recesses 134 may be provided with a cover 136 as shown in FIGS. 5 and 6 to protect the recess from unwanted particles.

The rigid spine of the socket systems described may have a flexible proximal aspect which allows for some flexibility of the rigid spine at the proximal end. Vertebrae similar to those used in the flexible spine may be used on the proximal end of the rigid spine to allow for easier flexion of the knee.

FIG. 7 depicts another embodiment of the adjustable socket system 410. The socket system 410 is similar to the socket system 110 and identical reference numerals are used to identify components of the socket system 410 similar to those of the socket system 110.

The socket system has a tensioner 128 for adjusting the tension and length of a tensioning element such as the cable 122. The socket system 410 has a circular guide 138 integrated into the interior of the posterior vertebrae 118 between each adjacent posterior vertebra 118 which guides the cable 122 through adjacent vertebrae. The circular guides 138 are preferably rotatable to increase the ease with which the tension of the cable 122 may be adjusted. It has been found that the preferred circular guides 138 enable using only one tensioner 128 while still maintaining easy adjustment of cable tension throughout the adjustable socket system 410. The circular guides may also be integrated into the interior of anterior vertebrae 116 or the anterior flaps 130 in place of the anterior guides 124 or the anterior guides 24. The circular guides 138 can be attached to the exterior of the anterior and posterior vertebrae as similarly shown in FIGS. 1-2 of the embodiments of the adjustable socket system described.

Figure 8:
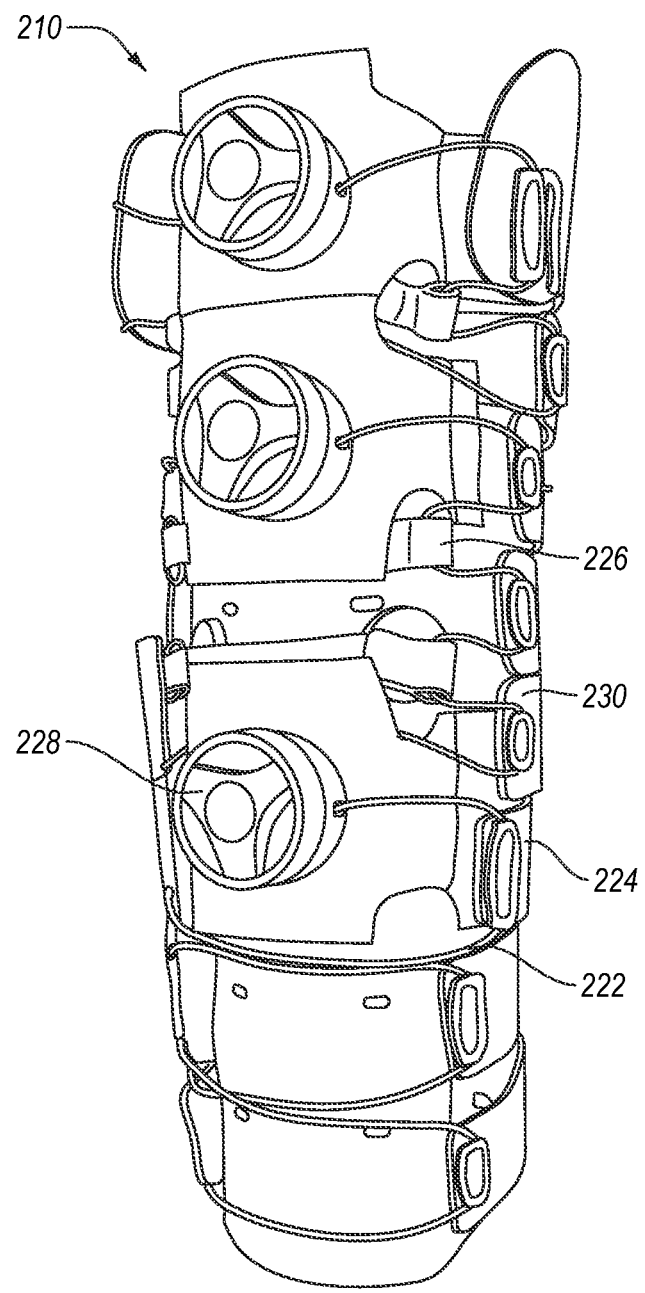
FIG. 8 is an elevational view of the posterior of another embodiment of the adjustable socket system.

FIG. 8 illustrates another embodiment of the socket system 210. The socket system 210 includes a flexible spine and rigid spine. The tensioners 228 are mounted on the rigid spine and connected to tensioning element 222. The anterior lateral flaps 230 have an exterior tensioning element guide 224 on the surface of the flap 230 near the posterior end of the flap 230. The posterior tensioning element guides 226 are flexible loops which may be made of textile extending from the rigid spine.

The regional circumference adjustment of embodiments of the adjustable socket system described is especially advantageous for disarticulation amputations in which the limb is separated at the joint. A disarticulation amputation has the advantage of naturally providing a good weight bearing and suspension surface for a socket system at and around the disarticulation. The tensioning system described provides the ability to allow easy donning and doffing while still providing good suspension. A tensioner may adjust the tensioning elements located just above the joint which would have a smaller circumference than the joint area. The socket system can be easily suspended and when donning or doffing is required the tensioner can adjust the length of the tensioning elements to enlarge the size of the socket.

This suspension system may also apply to condyles. Using flexible or semi-flexible material with different forms around and above the condyles such as the condylar wings, the tensioning system can similarly capitalize on the geometry of the condyles to provide additional suspension to the socket. Tension, which is applied over the flexible or semi-flexible material, is then added or removed to enable the entry or exit of the residual limb into the socket.

Similarly, the tensioning system comprising the tensioners, tensioning elements, and tensioning element guides may adjust the size of proximal area of the socket, the size of the socket brim. The socket may be a rigid socket having a semi-flexible proximal area to enable size adjustment for effortless entry and exit of the residual limb into and out of the socket. Such a socket provides improved suspension and comfort since the rigid brim is replaced with a semi-flexible brim which can be easily optimized by a prosthetist or the amputee. Another advantage of using a tensioning system is that the tension or pressure applied to the residual limb may be easily adjusted for improved comfort so that if the amputee knows that he or she will be inactive for periods of time the tension in the system can be decreased to allow for increased range of motion and comfort.

The tensioning system can facilitate donning and doffing of the prosthetic sleeve/liner and the prosthetic socket. Elderly or infirm patients may require assistance in inserting the residual limb worn with a prosthetic sleeve or liner into the prosthetic socket. Because of volume fluctuations experienced by all amputees, it is more difficult to don a socket when the volume of the residual limb is increased. The tensioning element may be attached to the residual limb where the tensioner is used to shorten the tensioning element and pull the residual limb into the socket. The tensioning element can have the form of a cable or wire, or the tensioner and/or tensioning element can be connected to an inner sleeve. Tensioning element guides may further form a pulley-like system to maximize the power and efficiency of the tensioner.

The embodiments of the socket system described preferably have a space between the distal end of residual limb and the distal end of the socket system. Distal padding or a distal cup can be used at the distal end within the socket systems to provide a cushion and distribution of pressure at the distal end of the residual limb such as a foam, silicone, or inflatable pad.

While the embodiments are described with respect to specific tensioning elements, a variety of tensioning elements may be used with the socket system including cables, wires, straps, laces, clips, clamps, or any other device used to provide and maintain tension as understood by the skilled person. Using the tensioning system described allows for faster, easier and finer adjustment of the socket system and quicker donning and doffing of the socket.

The embodiments of the pivoting vertebrae of the flexible spine described can also have a wide pivoting range and preferably have one to two degrees of freedom. The embodiments of the flexible spine described may also be in the form of piece of flexible material. Material may be added between to the flexible spine to provide additional stability to the flexible spine vertebrae.

The embodiments of the adjustable socket system as described have the feature of a rigid posterior spine and a flexible anterior spine. The adjustable socket system may also be implemented with a strut-like rigid posterior spine and rigid anterior spine to apply pressure to the residual limb using a tensioning element. The rigid anterior spine may be formed of interlocking vertebrae similar to those used on the rigid posterior spine in previous embodiments. At least one of the rigid spines can also be formed as a single continuous strut. The rigid spines may have openings or pins through which or around which the tensioning element is connected to the spines to define the circumference of the socket.

Like the rigid posterior spine described in previous embodiments, the rigid spines may have a predetermined angle regarding the longitudinal axis of the socket or the vertical axis. The rigid spine is manufactured at a certain angle by heating or bending the strut to a desired angle. Angling of the struts may be applied to any number of struts on the adjustable socket. Alternatively, the rigid spine can be manufactured, for example by milling or casting, at the predetermined angle. Heating or bending would not be required if the rigid spine is fabricated at the predetermined.

While the previous embodiments have been described as having a fully flexible anterior spine or a fully rigid anterior spine, various levels of flexibility in the anterior spine are advantageous to enable more customization options based on the needs of the user by varying the number of articulation points in the anterior spine. The anterior spine may have one articulation point.

FIG. 9 shows a frame of an embodiment of the adjustable socket having an anterior spine 234 formed of two rigid pieces 238, 240 which can rotate regarding each other and a posterior spine 236. The two rigid pieces 238, 240 can rotate regarding each other in a manner similar to the flexible spine as described above. Additional articulation points are added to change the flexibility of the anterior spine. The articulation points need not be evenly spaced from each other and can be closer together in certain portions of the spine to allow for greater flexibility in certain regions to better accommodate a residual limb which does not have an overall cylindrical shape or to accommodate a joint as in a transtibial amputation.

The previous embodiments have been described with two spines. Over two spines or struts may be used together to provide additional pressure distribution points in the adjustable socket and to better distribute the pressure on the residual limb.

FIG. 10A is a top schematic view of an adjustable socket 242 with two spines. FIG. 10B is a top schematic view of an adjustable socket 244 with three spines, and FIG. 10C is a top schematic view of an adjustable socket 246 with four spines. Each of the adjustable sockets 242, 244, 246 has a circumference 248 defined by a combination of distributing the spines and the tensioning element. Distributing the multiple spines around the circumference of the adjustable socket can be adjusted based on the needs of the user for structural stability and to accommodate the underlying anatomy and physiology of the residual limb.

Figure 11:
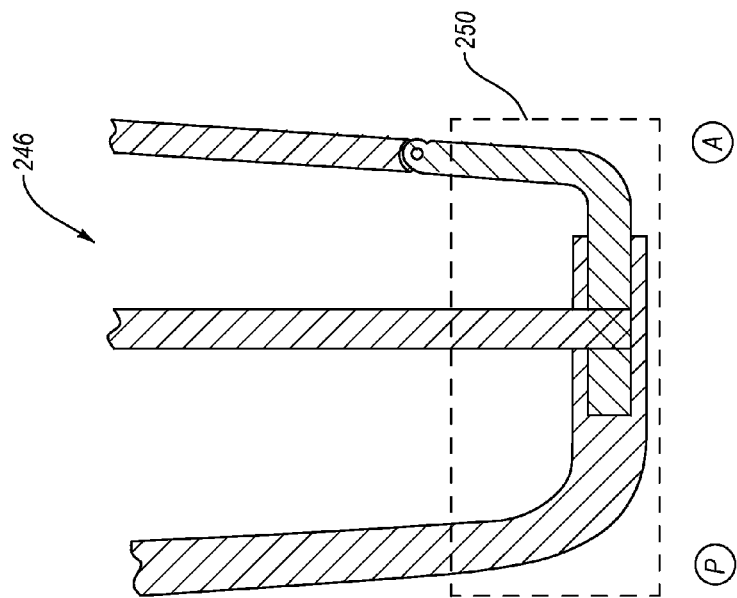
FIG. 11 is an elevational view of an embodiment of the adjustable socket system having four equally distributed spines.

FIG. 11 is a side view of the adjustable socket 244 with four spines. The spines can be connected at a distal base 250 to form an adjustable socket 244. The distal base 250 in FIG. 11 is formed through a combination of the distal ends of the spines. The distal base 250 may also be in a separate component to which the spines are connected.

Because spines or struts would apply more pressure to the residual limb, the embodiments of the adjustable socket described can have pressure release regions such that if struts apply significant force to the tissues of the residual limb, regions of pressure release to allow for tissue displacement. The release regions may be in openings in the socket, soft elastically deformable material, or stiff material having regions that are elastically deformable. The release regions can also be a recess on the stiff material to prevent application of pressure to an area of the residual limb. The aim is to create even pressure distribution using the flexible plastic sheet under the spines to distribute a load from spines and the tensioning element. This arrangement prevents the amputee from feeling the spines as points of pressure. Due to tensionsing elements and careful material selection, it is possible to achieve uniform quasi-hydrostatic pressure. As an alternative, uneven pressure distribution can be likewise achieved.

Figure 12:
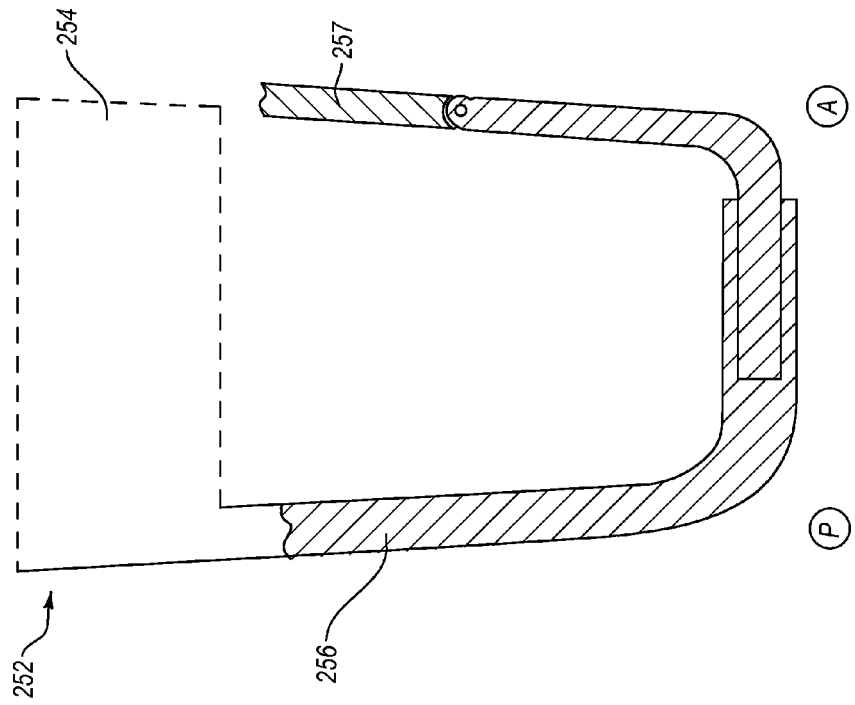
FIG. 12 is a schematic side view of an adjustable socket system having a rigid posterior spine, a rigid anterior spine, and a brim.

FIG. 12 shows an embodiment of the adjustable socket 252 with a brim 254. The brim 254 is connected to the proximal end of a posterior spine 256 to allow for proximal loading and proximal stability of the adjustable socket on the residual limb. The brim 254 may also be connected to the proximal end of an anterior spine 258 to enable even distribution of loading and consistent stability around the proximal end of the adjustable socket 252. When a brim is used on an adjustable socket having over two spines or struts such as those shown in FIG. 10A-10C, the brim may be connected to the proximal end of many the spines for different levels of proximal loading and stability. The brims can also be used with any level of amputation.

Figure 14:
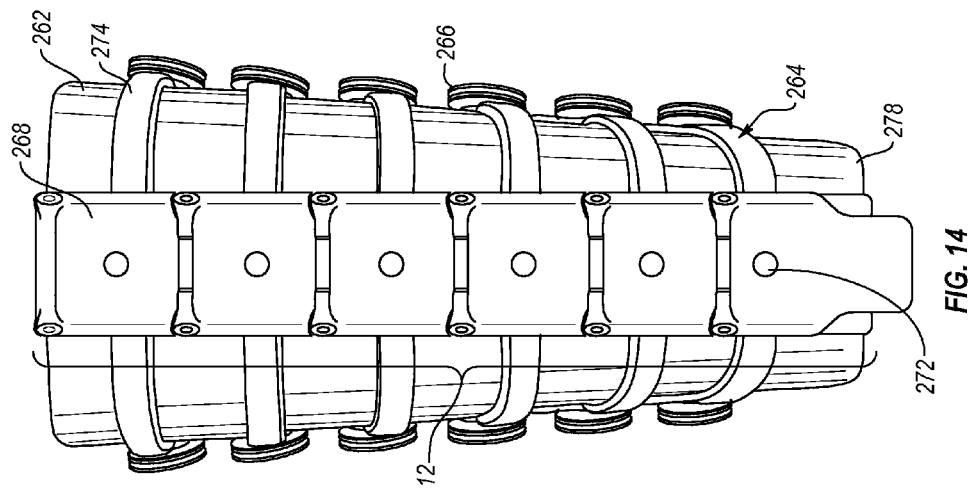
FIG. 14 is an elevational view of the anterior side of the adjustable socket system of shown in FIG. 13.
Figure 13:
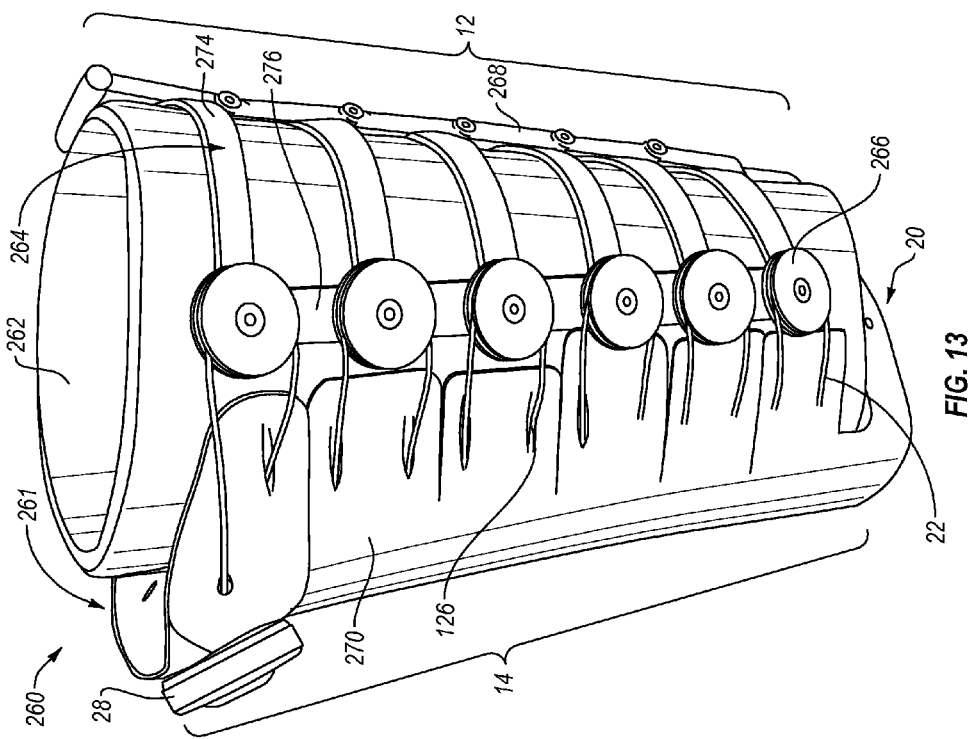
FIG. 13 is a perspective view of the side of an adjustable socket system having a socket frame and a tubular insert.

FIGS. 13 and 14 show another version of the adjustable socket system 260. FIG. 13 is a side perspective view of the adjustable socket system 10, and FIG. 14 is a front elevational view of the socket system 260. The adjustable socket system 260 includes an adjustable socket frame 261, a tubular insert 262, and a tensioning system. The tensioning system and the adjustable socket frame 261 provide a clamping mechanism to apply pressure to the residual limb received in the tubular insert 262 by adjust the circumference of the tubular insert 262. Through the adjustability and flexibility provided by the socket system 260 as a whole and its individual components, the socket system 260 provides the user with a customizable socket which can conform to the shapes of each user's residual limb.

The adjustable socket frame 261 includes an anterior spine 12, a posterior spine 14, and an adjustable base 20 similar to other socket systems described. The anterior spine 12 is flexible and is formed of a plurality of individual interlocking vertebrae 268 which can pivot regarding each other. The posterior spine 14 is rigid and formed of a plurality of individual interlocking vertebrae 270 which form a stable, non-pivoting connection with each other. The individual interlocking, non-pivoting vertebrae 270 may be identical to vertebrae of the rigid spine described previously with shorter lateral flaps or extensions. The individual interlocking, pivoting vertebrae 268 may be identical to vertebrae of the flexible spine described previously without lateral flaps or extensions.

The tubular insert 262 is received within the socket frame 261. The tubular insert 262 has an open proximal end to receive a residual limb, and the distal end may be open or closed. The tubular insert 262 defines the interior surface of the socket system 260 such that the tubular insert 262 is the interface between a residual limb and the socket frame 261.

The tubular insert circumferentially forms the interior surface of the system 10. The ends of the sheet of flexible material are brought towards each other to give the insert 262 a tubular shape that is used in a transtibial arrangement. The meeting point of the ends of the sheet is preferably arranged at the posterior side of the socket frame 261. Forming the tubular insert 262 from a sheet of material advantageously allows the socket system 260 to be bifurcated to create an enlarged opening to receive the residual limb. This bifurcation enables easier donning of the socket system 260.

For transfemoral or other levels of amputation outside of transtibial, the meeting point can be in any position. The meeting point can be chamfered or the overlap region can be formed from different or softer material. The meeting point (overlap) can be further enhanced by changing the edges to be waved, oblique or other arrangements to decrease possible pressure points.

The tubular insert 262 of socket system 260 may be formed of a sheet of flexible material, preferably a polymeric material such as silicone. The tubular insert 262 may be provided with a coating on its outer surface to reduce the coefficient of friction between the tensioning element 22 and the tubular insert 262. The tubular insert 262 can have an outer textile layer and inner silicone layer or be coated with a matting agent on its outer surface. Alternatively, a soft or low density polyethylene may be use which is semi-flexible but preferably does not stretch.

The tensioning system of the socket system 260 includes tensioner 28, the tensioning element 22, and a plurality of tensioning element guides 266. The tensioning element guides 266 are arranged longitudinally in a column on the tubular insert 262. An anterior enclosure 264 may be in the tensioning system. The tensioning element guides 266 are attached to both the tubular insert 262 and an anterior enclosure 264 extending laterally from the anterior vertebrae 268 of the flexible spine 12. The socket system 260 is shown with the preferred one-to-one correspondence between the anterior vertebrae 268 of the flexible spine 12 and the posterior vertebrae 270 of the rigid spine 14. Tensioning element guides 266 are provided for each vertebra 268, 270 pair and are positioned circumferentially between the vertebrae 268, 270 on either side of the spines 12, 14. The vertebrae 268, 270 and the tensioning element guides 266 are preferably laterally aligned.

The tensioning element 22 is alternately threaded around a tensioning element guide 266 and through a posterior guide 126 in the posterior vertebra 270. The posterior vertebra 270 may have an internal tensioning element guide similar to guide 138 in FIG. 7 of the socket system 310. Each internal tensioning element guide 138 is laterally located approximately between each tensioning element guide 266 to provide tensioning continuously along the length of the socket system.

The anterior enclosure 264 forms the outermost portion of the anterior area of the socket system 260. The anterior enclosure 264 includes a lateral member 274 which may have an elongate shape. The lateral member 274 attaches at a first end to pivoting vertebrae 268 and at a second end connect to the tensioning element guide 266 corresponding to those pivoting vertebrae 268. At the second end, the lateral member 274 is connected between the tensioning element guide 266 and the tubular insert 262. The enclosure 264 has a longitudinal member 276 connecting each lateral member 276 between each tensioning element guide 266 to an adjacent later member 276. The anterior enclosure 264 has a central member 278 having approximately the same dimensions as the anterior spine 12. The lateral members 274 extend laterally from either side of the central member 278. The anterior enclosure is made of a flexible material preferably a polymeric material such as silicone or rubber.

The tubular insert 262 and the anterior enclosure 264 are attached to each individual anterior vertebra 268 using a connector 272 such as a screw, rivet, or weld nut. The central member 278 of the anterior enclosure 264 is positioned between the anterior spine 12 and the tubular insert 262.

The tensioning element guides 266 and posterior guides 138 are preferably rotatable to ease the adjustment of the tensioning element 22 length and distribute pressure evenly throughout the length of the socket system 260. To enable rotation of the tensioning element guides 266, the guides 266 are preferably attached to the enclosure 264 with a central weld nut, screw, rivet, or pin. To decrease the coefficient of friction between the guides 266 and the enclosure 264, a washer is placed between the guide 266 and the enclosure 264. The washer is made of textile such as nylon or of metal.

The tensioner 28 is mounted on the posterior spine 14 and controls the length of the tensioning element 22 to adjust the circumferential size of the tubular insert 262. The combination of the tensioner 28, the tensioning element 22, the guides 266, and the anterior enclosure 264 arranged on the frame 261 change the circumferential size of the tubular insert 262 to adjust the fit of the socket system 260 on the residual limb of the user.

Although the anterior enclosure 264 is described as being a separate component of the socket system 260, the anterior enclosure 264 may be integrated into the tubular insert 262 by molding the tubular insert 262 to be thicker in areas of the tubular insert 262 which would correspond to the relative positions of the lateral members 274, longitudinal members 276, and central member 278 regarding the tubular insert 262. The tubular insert 262 is reinforced in areas corresponding to the components of the anterior enclosure 264.

Turning to the socket system 280 in FIGS. 15-17, FIG. 15 is a side elevational view of the socket system 280. FIG. 16 is an elevational view of the anterior of the socket system 280, and FIG. 17 is an elevational view of the posterior of the socket system 280. Similar to socket system 260, the socket system 280 has an adjustable socket frame 261, a tubular insert 262, and tensioning element guides 266. The socket frame 261 has an anterior flexible spine 12, a posterior rigid spine 14, and a distal base 20, and the socket frame 261 is fitted around the tubular insert 262. Similar to socket system 260, the tubular insert 262 is attached to each anterior vertebra 268 with a connector 272 such as a weld nut or screw.

The tensioning element guides 266 are attached to either side of the tubular insert 266 between the anterior spine 12 and the posterior spine 14. The area on the tubular insert 262 in which the tensioning element guides 266 or the anterior vertebrae 270 are attached may be a reinforced area 292 to strengthen the attachment point on the tubular insert 262. The area 292 may be reinforced with a reinforcement layer or the area 292 may be provided with a greater thickness. To attach the tensioning element guides 266 and the anterior vertebrae 270 to the tubular insert 262, the tubular insert 262 is provided with openings 290 at the connection point.

The tensioning element 22 is threaded through posterior guide 126 in each posterior vertebra 270 and around a circular guide 138. The tensioning element 22 exits another posterior guide 126 and is looped around a tensioning element guide 266. The tensioning element 22 is connected to the tensioner 28, and the tensioner 28 controls the length of the tensioning element 22 to adjust the circumferential size of the tubular insert 262.

The socket frame 261 may be formed of a solid rigid material such as plastic or metal. To add some breathability to the socket system 280, the vertebrae 270 can have perforations 292 which allow air to circulate between the socket frame 261 and the residual limb and/or tubular insert 262.

Figure 18:
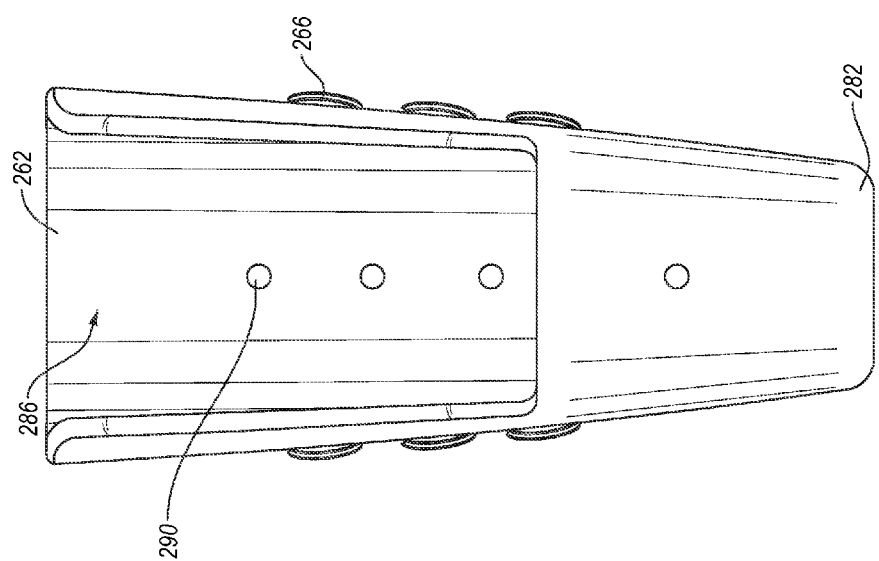
FIG. 18 is an elevational view of from the posterior side of a tubular insert.
Figure 20:
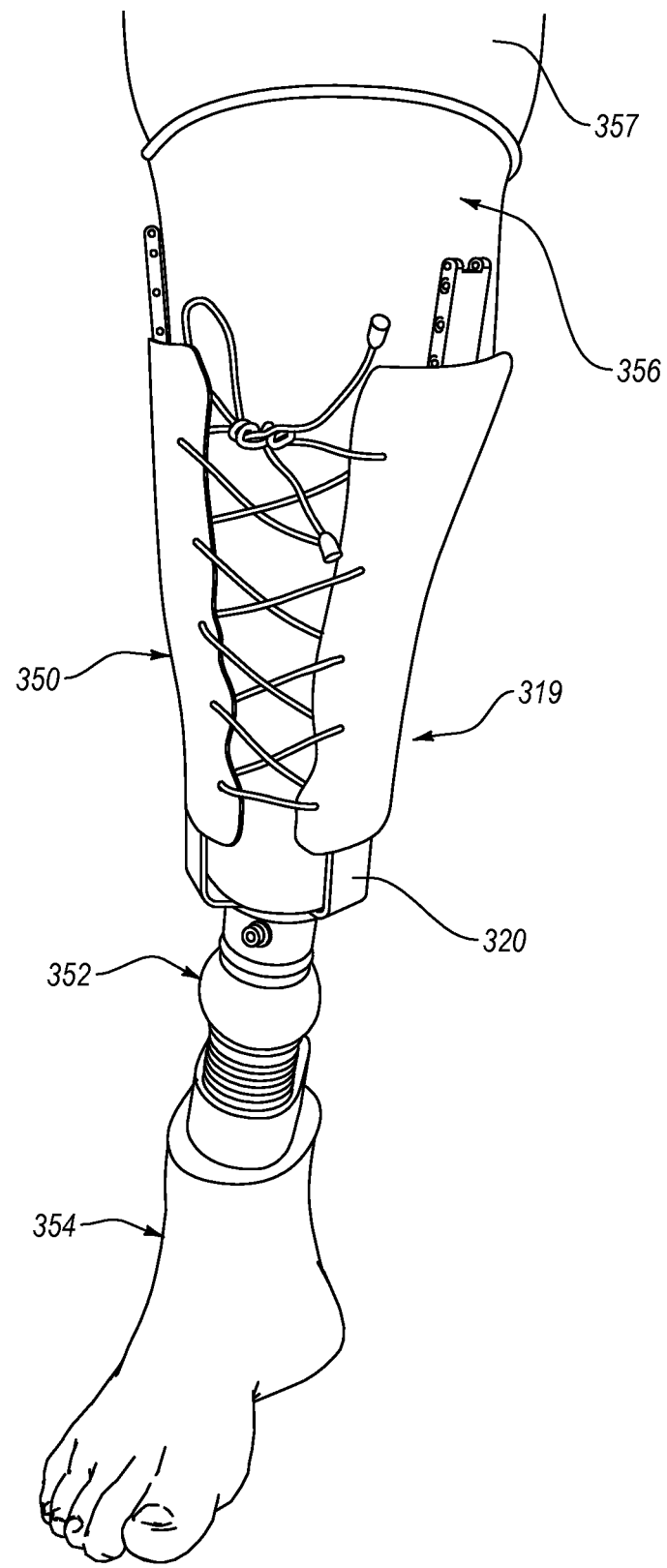
FIG. 20 is a perspective view of another embodiment of an adjustable socket system.
Figure 21:
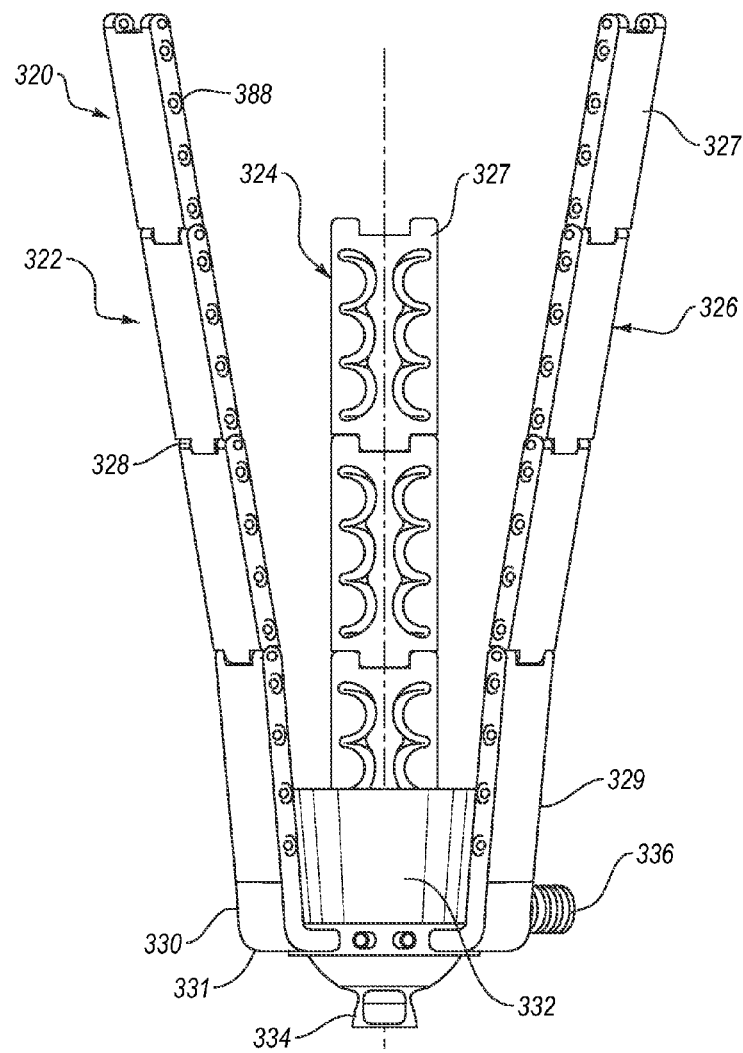
FIG. 21 is an elevational view of a frame for the adjustable socket system in FIG. 20.
Figure 22:
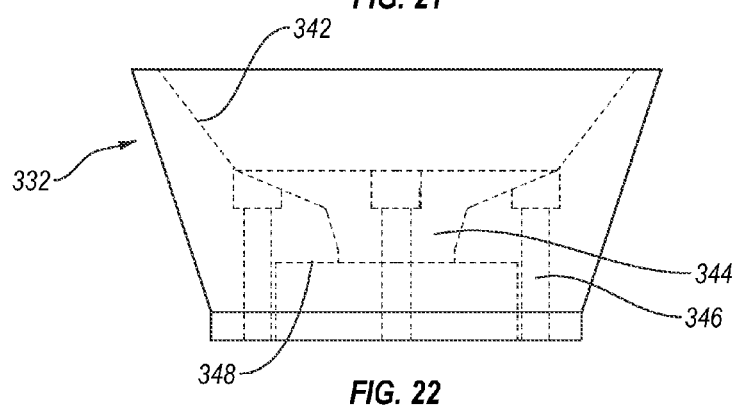
FIG. 22 is an elevational view of a distal end piece of the adjustable socket system in FIG. 20.

FIG. 18 shows an elevational view of the tubular insert 262 of FIGS. 15-17 fitted with tensioning element guides 266 from the posterior of the tubular insert 262. The tubular insert 262 has an open proximal end to receive a residual limb and a closed distal end. The tubular insert 262 has openings 290 for attaching to vertebrae or tensioning element guides 266.

The tubular insert 262 may be provided with a cutout area 286 on the side corresponding to the tensioning element side of the socket system. The cutout area 286 enables a better fit to the residual limb when the tensioning element 22 decreases the circumference of the tubular insert 262 by bringing each side of the cutout area 282 closer to each other. The cutout area 282 also enables the user to more easily don the socket system 280 by enabling the proximal end of the tubular insert 262 to be enlarged. Since the anterior spine 12 is flexible, the socket system 280 can be bifurcated while attached to the tubular insert 262.

The tubular insert 262 also has distal padding 282 to provide a cushion between the distal end of the residual limb and the base 20 of the socket frame 261.

Alternatively, the tubular insert 262 may be a tubular prosthetic liner adapted to be used with socket frame 261 by attaching tensioning element guides 266 to the prosthetic liner and removing a portion of the posterior side of the prosthetic liner. An example of a prosthetic liner which can be adapted to be used with socket frame 261 is the prosthetic liner described in U.S. Pat. No. 8,123,818 issued on Feb. 28, 2012 belonging to the assignee of this disclosure and incorporated by reference.

A tubular insert 262 having a stiffened or strengthened anterior area 292 can also be used with a socket frame 261 lacking an anterior spine 12.

Figure 19:
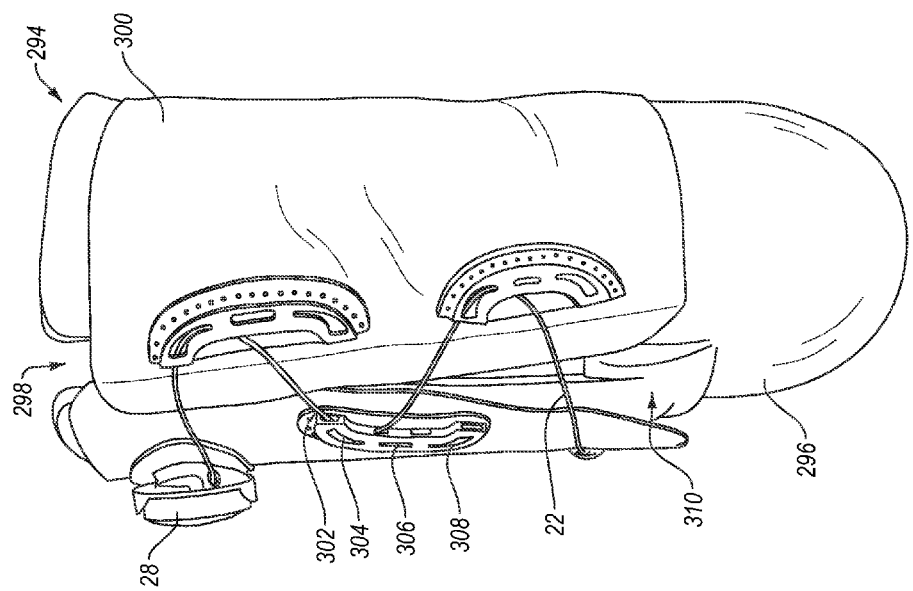
FIG. 19 is an embodiment of an adjustable socket system.

FIG. 19 shows a socket system 294 where a socket 296 is provided with an outer sleeve 300 fitted around the outer surface of the socket 296 to adjust the circumference of the socket 294. The socket 296 has an open proximal end to receive a residual limb and a closed distal end. The tensioner 28 is attached to the sleeve 300 and the tensioning element 22 is threaded through curved guides 302 on the opposed ends of the sleeve 300. The sleeve 300 is formed of a continuous sheet of material, and the curved guides 302 are attached near the edge of opposite ends of the sheet material to form a cylindrical shape when placed on the socket 296.

To facilitate the adjustment of the circumference of the socket 296, the socket 296 is formed from a rigid and elastically deformable material, and the socket 296 is strategically weakened to enable easier adjustment of the volume of the socket 296. To strategically weaken the socket 296, the socket 296 can be provided with longitudinal cutouts or openings 298 in the surface of the socket 296 in the posterior region of the socket near the longitudinal adjustment area 310 of the sleeve 300.

The tensioning element 22 can enter and exit several different partial areas on the curved guide 302 to change the number of crossings and location of crossings between the two ends of the sleeve 300. This flexibility provides the user with the ability to adjust the area in which more tension and less tension applies to the socket 300. As seen in FIG. 19, the tensioning element 22 is threaded through a proximal area 304 of the curved guide 302. The tensioning element 22 can also be threaded through any combination of the proximal area 304, the central area 306 and the distal area 308 of the curved guide 302.

The socket 296 may be a hard socket adapted to be used with sleeve 300 through the strategic weakening of the socket 296 as described.

Although the embodiments of the socket system are described with respect to a transtibial level amputation, the socket system may be used with a transfemoral level amputation as well. In an embodiment of a transfemoral socket system, the lateral surface of the transfemoral socket system forms the weight bearing structural element while the medial surface comprises apertures which may be used in combination with tensioning elements to form a flexible surface.

From the features of the adjustable socket system described above, an adjustable socket system is provided that provides simple and quick adjustment to the volume and shape of the socket system, and hence to a residual limb supported by the socket system. The socket system departs from the conventional static socket type and instead allows for adjustment in height, volume and shape permitting adjustment to assure stable fitting of the socket. Further, the socket system accommodates a variety of differently sized residual limbs, and is not constrained to a particular amputee but can be used by a variety of amputees. The socket system is highly breathable enabling better air circulation in the cavity of the socket.

Referring to the embodiment of FIGS. 20-23, another embodiment of an adjustable socket system 319 includes a frame 320, and a sleeve device 350 extending over portions of the frame 320. The adjustable socket system 319 is used in combination with a pylon/shock absorber 352, a prosthetic foot 354 with a cosmesis, and a liner 356 extending over the residual limb 357.

The frame 320 defines at least three sets of elongate segments 322, 324, 326 extending from a base 330 of the frame. The base 330 connects to each set of elongate segments 322, 324, 326, and receives a distal end piece 332. A pyramid adapter 334 or similar adapter extends from the base 330 to couple to the pylon 352. A pin lock 336, such as ICELOCK 400 series sold by Ossur hf of Reykjavik, Iceland, may be received by the distal end piece.

The base segment 329 connecting adjacent to the base 330 secures to a generally bent element 331 directing the elongate segments 322, 324, 326 longitudinally from the base 330. The base segment 329 may be rigidly connected to the base element, or alternatively pivotally connected. The segments 327 connecting above the base segment 329 are pivotally connected to one another at pivot locations 328, thereby allowing the frame 320 to adapt the shape of an individual residual limb.

The segments 327 may define a plurality of interior channels 324 (or alternatively exterior channels) for receiving a cable or plurality of different cables connected to a dial tensioning mechanism, as discussed above. Apertures 338 are provided for permitting the cable to extend through so the cable can be laced among the various elongate segments.

The segments and the frame may be constructed from reinforced carbon fibers to enable flexure, and may be adapted in various thickness and lengths according to the demands of a particular amputee. Alternatively, for improved stiffness, the segments may be constructed from metal, such as aluminum.

Regarding the distal end piece 332, by using knowledge of stump and liner profiles, the distal end piece may be able to accommodate most amputees. For example, the distal end piece 332 defines an interior contour 342 for receiving the distal end of a residuum. The distal end piece 332 may be configured to receive a suspension mechanism, such as a pin lock. The distal end piece 332 includes a recess 344 for receiving a pin extending from a liner, and a cavity 348 and channels 346 for receiving part of an adapter.

Figure 23:
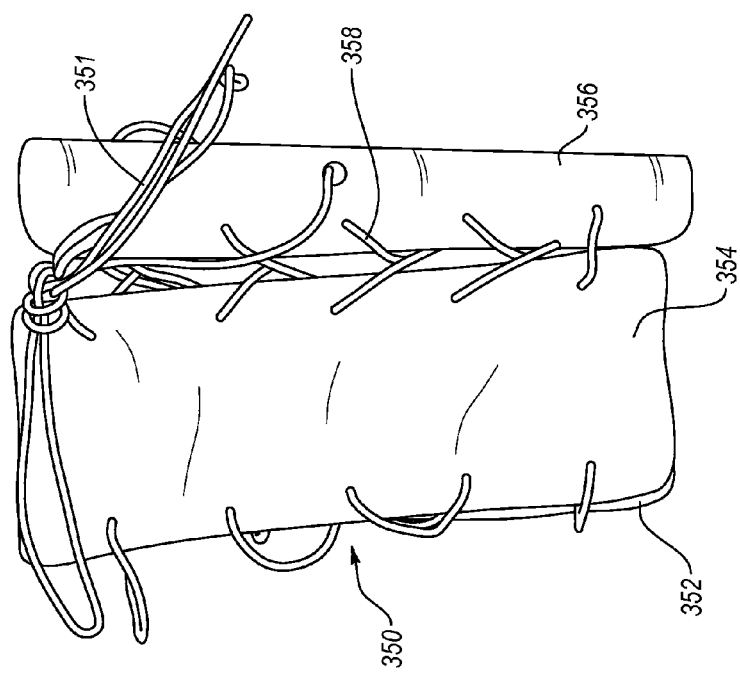
FIG. 23 is an elevational view of a tightening sleeve of the adjustable socket system in FIG. 20.

FIG. 23 exemplifies a sleeve 350 as an alternative or in supplement to using cabling for securing the elongate segments of the frame to the residuum. The sleeve 350 includes pockets 352, 354, 356 corresponding to each set of elongate segments, and a central lacing system 351 connecting the pockets 352, 354, 356 to one another. The pockets may be individually separate from one another, and solely connected to one another by the lace. In use, the user can slide the pockets over the frame and tension the lace so as to secure the frame on the residuum. The textile forming the pockets is preferably non-stretchable, although not limited to non-stretchable material.

Figure 24:
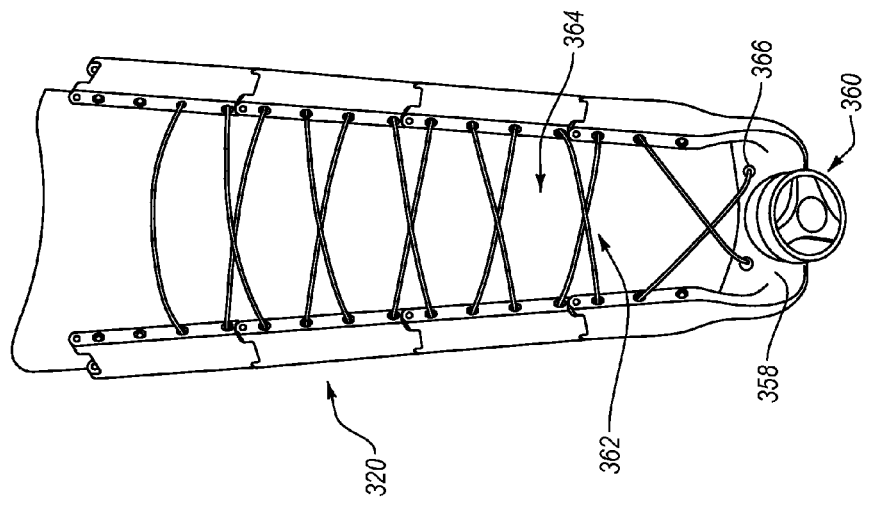
FIG. 24 is an elevational view of another embodiment of an adjustable socket system.
Figure 25:
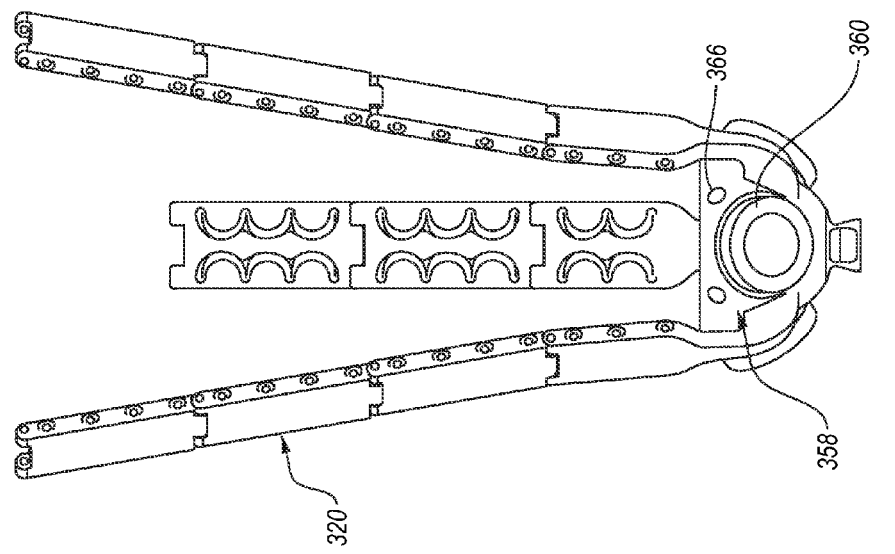
FIG. 25 is an elevational view of a frame for the adjustable socket system of FIG. 24.

Referring to the embodiment of FIGS. 24 and 25, the frame 320 is provided with a plurality of cables 362 connected to at least one tensioning device 360, such as a rotary or dial tensioning device. Multiple dial tensioning devices may be used, as shown in FIG. 25 by the use of three dial-tensioning devices. The distal end piece 358 is adapted to receive the dial tensioning devices, and may include channels 366 adapted for the cables to extend therethrough. A liner 364 is used to cover the residuum and prevent any cutting by the cables. The cables may be covered or have protective covering them so as to distribute pressure better and avoid any damage to the liner or residuum.

Figure 26:
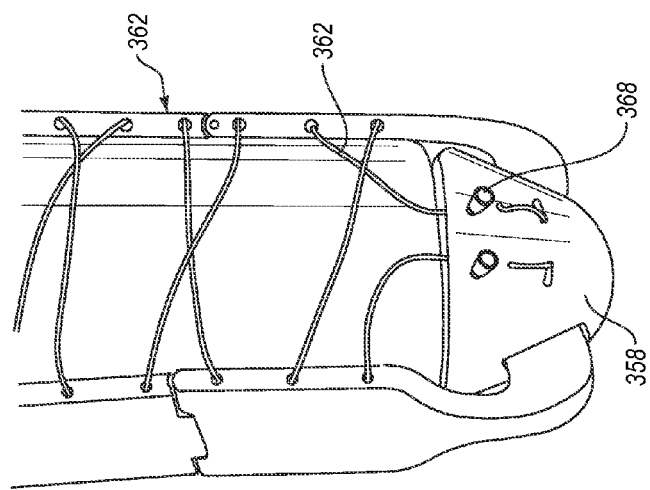
FIG. 26 is a schematic view showing an alternative of the frame in the embodiment of FIG. 24.

In an alternative to the embodiment of FIGS. 24 and 25, FIG. 26 shows frame 320 with the dial tensioning devices removed. In this embodiment, set screws 368 are used to maintain the cable 362 in a fixed position.

2. Embodiments of the Adjustable Pylon and Adjustable Prosthetic Foot

Under an embodiment of an adjustable prosthetic limb system, FIG. 27 shows the adjustable prosthetic limb system having an adjustable socket 402, an adjustable pylon 404, and an adjustable foot 406. The adjustable pylon 404 has an adjustable length and shape and enables the position of the socket 402 and foot 406 to be adjusted relative to each other in various directions. The positions of the socket and foot relative to each other may be adjusted through specific positioning of each component at the ends of the pylon 404 or through the shape of the pylon 404.

FIG. 27 shows the pylon 404 as having a linear, cylindrical shape and as formed from at least one stacking component 411. Additional stacking components can be attached to each other to increase the length 408 of the pylon 404 to allow the prosthetic limb system to be adjusted to different user heights and amputation levels.

FIG. 28 shows an embodiment of a single stacking component 411. The stacking component 411 has the form of a circular disc or ring and has a proximal connecting portion 422 and a distal connecting portion 424. The distal connecting portion 424 of the stacking component 411 is received in the proximal connecting portion 422 of a second stacking component 412.

The proximal connecting portion may be in a circular recess having a continuous side wall to receive the distal connecting portion 424 having the shape of a circular disc. The stacking components are interlocked with each other using a locking mechanism such as a spring-loaded pin inserted through the openings 426 of the stacking component 411 and the openings 428 of the stacking component 412. Other types of locking mechanisms which allow for the removal and reattachment of the stacking components to each other may be used, such as snapping parts or set screws.

The alignment between the socket 402 and the prosthetic foot 406 can be simultaneously adjusted when adjusting the length 408 of the pylon 404 by using stacking components which have the proximal connecting portion 422 offset from the distal connecting portion 424. The center of the proximal connecting portion 422 can be shifted in the horizontal plane a certain distance from the center of the distal connecting portion 424. Each stacking part may have a different offset such as a 3 mm, 5 mm, or 10 mm offset.

FIG. 27 shows the surfaces of the proximal connecting portion 422 and the distal connecting portion 424 to be parallel to provide a foot which has an angle perpendicular to the pylon. The adjustable pylon 404 is further advantageous since the stacking components can adjust the tilt angle of the foot regarding the horizontal axis. To tilt the angle of the prosthetic foot 406, stacking components may be used which have an angle offset from distal to proximal. This may be achieved by varying the thickness of the distal connecting portion 424 from the posterior to the anterior. The adjustable pylon can also be used with a wedge or shim to change the tilt angle of the foot 406 and/or the socket 402.

Because a variety of stacking components with different combinations of horizontal and/or tilt angle offsets can form the adjustable pylon 404, the prosthetist and user are presented with many options to customize the adjustable prosthetic limb system to the needs and preferences of the user. The adjustable pylon 404 may be provided to the prosthetist or user in a kit with a variety of stacking components, the adjustable socket, and the adjustable foot 406.

It is further preferred the adjustable socket be used with an adjustable prosthetic foot since the length of the foot also affects the gait of the user. The adjustable foot may be used with or without a pylon or an adjustable pylon. The adjustable prosthetic foot 406 of the prosthetic limb system has an adjustable length in two parts which are movable or slide relative to each other. The adjustable foot 406 has an anterior or forefoot part 414 and a posterior or hindfoot part 418. The anterior part 414 has a toe portion 434 and protruding midfoot portion 416 inserted into a recess 420 of the posterior part 418.

As shown in one embodiment of the adjustable foot 406 in FIG. 29, the protruding midfoot portion 416 has a plurality of adjustment points distributed along the midfoot portion to adjust the length at which the anterior part 414 extends from the posterior part 418. The adjustment points may be in recesses or openings which receive a corresponding locking part to lock the anterior part 414 in place. The anterior part 414 may be locked in place using other mechanisms such as a releasable clamping mechanism on the protruding midfoot portion 416.

The clamping mechanism may be used in combination with corresponding recesses distributed along the length of the protruding midfoot portion to more stably maintain the length of the adjustable foot. The anterior part 414 and the posterior part 418 can also be adapted to allow for adjustability of the angle of the forefoot part 414 regarding the ground or the angle of the forefoot part 414 regarding the posterior part 418.

Alternatively, the adjustable property of the foot 406 may be achieved using stacking components similar to those used in the pylon 404 alone or in combination with a sliding adjustment as described regarding FIG. 29. Using stacking components in the foot 406 provides the advantage of a linear translation and/or an angular translation from one piece to another. The stacking components used in the foot can lengthen the foot and/or to change the angle of the anterior part 414 regarding the posterior part 418.

Using stacking components in the foot 406 provides an additional adjustable feature. A stacking member would enable an amputee with a high heeled shoe to obtain the correct angle from the heel to the toe. The overall angle of the foot 406 can be adjusted using the stacking components 411. Using stacking components in the foot 406 provides the user an additional point that can adjust the overall angle of the foot 406 by changing the overall shape of the foot 406 to better approximate the shape needed by the user.

FIG. 27 also shows the bottom 430 of the toe portion 434 and the heel area 432 of the posterior part 418 as formed of a different material than the remainder of the prosthetic foot 406 to provide additional support to the user on a heel strike and toe-off since these areas are subjected focused pressure and weight during gait. These areas 430, 432 may be formed of a material having stronger properties to strengthen durability of the foot such as a material having a high durometer.

The material used in these areas 430, 432 can also have a low durometer to provide some shock absorption in the heel or toe area. The materials used in the areas 430, 432 may be a plastic or an elastomeric material such as rubber. The areas 430, 432 can have regions within the area 430, 432 softer than others to allow the user to more easily fit the adjustable foot 406 into a shoe. The areas 430, 432 may also be removable or replaceable to provide the user with more customization and to enable the replacement of worn areas on the adjustable foot 406. The areas 430, 432 can also be molded with the foot 406.

The embodiments of the adjustable prosthetic limb system described may be used with a liner as described in U.S. Pat. Nos. 8,123,818 and 7,118,602 or a rigid dressing as described in U.S. Pat. No. 7,094,212 all of which are incorporated by reference and belong to the assignee of this disclosure.

The embodiments of the adjustable prosthetic limb system described may be used with a prosthetic foot as described in U.S. Pat. No. 8,007,544 incorporated by reference and belonging to the assignee of this disclosure.

C. Conclusion

The embodiments of the prosthetic limb system as described possess the feature of a wide range of adjustability and adaptability through individual elements which each possess a large range of adjustability and adaptability to different user needs. An advantageous result of this adjustability and adaptability of parts customized to the user's needs are not required. Therefore, the adjustable prosthetic limb system provides the user with a prosthetic limb system that adapts to a wide range of user needs and preferences while making it unnecessary to measure and wait for customized parts and provides a complete, instant prosthetic limb solution.

While the foregoing embodiments have been described and shown, alternatives and modifications of these embodiments, such as those suggested by others, may be made to fall within the scope of the invention. The principles described may be extended to other types of prosthetic or orthopedic devices.

The invention claimed is:

1. An adjustable socket system adapted for securing a prosthetic device to a residual limb during gait, the system comprising:
   a distal end portion;
   a frame having a plurality of elongate fingers longitudinally extending from the distal end portion, each elongate finger defining at least two segments connected to one another at an adjoining hinge and extending in a longitudinal direction relative to the distal end portion, the adjoining hinge connecting a proximal end section of a respective one of the segments to a distal end section of another respective one of the segments;
   an axis extending along a length of the frame between the distal end portion and a proximal end of the frame, the at least two segments arranged to hinge perpendicular to the axis;
   at least one elongate element connecting to the plurality of fingers and forming part of a circumference of the adjustable socket system in combination with the plurality of fingers, the at least one elongate element having a flexible configuration; and
   at least one tensioning device mounted to the distal end portion below frame and to the at least one elongate element, the at least one tensioning device operable to adjust a length of the at least one elongate element.

2. The system according to claim 1, wherein the distal end portion defines a plurality of base elements extending laterally and extending longitudinally in part to couple to a respective one of the segments of each of the plurality of fingers.

3. The system according to claim 2, wherein the plurality of base elements are rigidly secured to the respective one of the segments of each of the plurality of fingers.

4. The system according to claim 1, wherein the distal end part has a proximal contour adapted to receive a distal end of a residual limb.

5. The system according to claim 1, wherein the at east one tensioning device comprises a dial tensioner.

6. The system according to claim 1, wherein the at least two segments define a plurality of channels for directing the at least one elongate element along a surface of the at least two segments.

7. The system according to claim 6, wherein the at least two segments defines opposed apertures corresponding to opposed side walls and in communication with a respective one of the plurality of channels, the at least one elongate element extending through the opposed apertures.

8. The system according to claim 1, wherein the plurality of fingers is formed from a flexible material.

9. The system according to claim 1, wherein the at least one elongate element has at least one end adjustably secured to the distal end portion, adjustment of the at least one elongate element is arranged to change tension in the at least one element.

* * * * *